(12) United States Patent
Skudas et al.

(10) Patent No.: US 10,457,720 B2
(45) Date of Patent: Oct. 29, 2019

(54) ROBUST ANTIBODY PURIFICATION

(71) Applicant: Merck Patent GmbH, Darmstadt (DE)

(72) Inventors: Romas Skudas, Mainz (DE); Matthias Joehnck, Muehltal (DE); Bianca Edelmann, Pfungstadt (DE); Simon Braun, Heusenstamm (DE); Mikhail Kozlov, Lexington, MA (US); Matthew T. Stone, Cambridge, MA (US); Kevin Galipeau, Westford, MA (US)

(73) Assignee: Merck Patent GmbH, Darmstadt (DE)

( * ) Notice: Subject to any disclaimer, the term of this patent is extended or adjusted under 35 U.S.C. 154(b) by 270 days.

(21) Appl. No.: 15/123,110

(22) PCT Filed: Feb. 18, 2015

(86) PCT No.: PCT/EP2015/000361
§ 371 (c)(1),
(2) Date: Sep. 1, 2016

(87) PCT Pub. No.: WO2015/131978
PCT Pub. Date: Sep. 11, 2015

(65) Prior Publication Data
US 2017/0073394 A1 Mar. 16, 2017

Related U.S. Application Data

(60) Provisional application No. 61/947,761, filed on Mar. 4, 2014.

(51) Int. Cl.
| | |
|---|---|
| *B01D 15/32* | (2006.01) |
| *B01D 15/36* | (2006.01) |
| *B01D 15/38* | (2006.01) |
| *C07K 1/20* | (2006.01) |
| *C07K 16/00* | (2006.01) |

(52) U.S. Cl.
CPC ............ *C07K 16/00* (2013.01); *B01D 15/327* (2013.01); *B01D 15/361* (2013.01); *B01D 15/3809* (2013.01); *C07K 1/20* (2013.01)

(58) Field of Classification Search
None
See application file for complete search history.

(56) References Cited

U.S. PATENT DOCUMENTS

| | | | | |
|---|---|---|---|---|
| 8,946,395 | B1 * | 2/2015 | Herigstad | C07K 1/20 530/412 |
| 9,783,570 | B2 | 10/2017 | Baehner et al. | |
| 9,994,609 | B2 * | 6/2018 | Ghose | C07K 1/20 |
| 2005/0136521 | A1 * | 6/2005 | Shukla | C07K 1/20 435/183 |
| 2013/0131318 | A1 | 5/2013 | Kremer et al. | |
| 2017/0340989 | A1 * | 11/2017 | Skudas | C07K 1/20 |

FOREIGN PATENT DOCUMENTS

| | | |
|---|---|---|
| JP | 2013519652 A | 5/2013 |
| WO | 03102132 A2 | 12/2003 |
| WO | 13004587 A1 | 1/2013 |

OTHER PUBLICATIONS

Tosoh Corporation, Instruction Manual for Toyopearl HIC Type, copyright 2007 (Year: 2007).*
International Search Report dated Jul. 23, 2015 issued in corresponding PCT/EP2015/000361 application (5 pages).
Written Opinion of the International Searching Authority dated Jul. 23, 2015 issued in corresponding PCT/EP2015/000361 application (12 pages).
E.G. Spack et al., "Hydrophobic Adsorption Chromatography to Reduce Nonspecific Staining by Rhodamine-Labeled Antibodies", Analytical Biochemistry, vol. 158 (1986) pp. 233-237.
J.K. Odonnell et al., "Purification of Monoclonal Antibodies Using New Pore Size Optimized HIC Resins", Bioprocess International Show & Exhibition (Nov. 6, 2006) pp. 1-18.
H. F. Liu et al., "Recovery and Purification Process Development for Monoclonal Antibody Production", MABS, vol. 2, No. 5 (2010) pp. 480-499.
S. Ghose et al., "Purification of Monoclonal Antibodies by Hydrophobic Interaction Chromatography Under No-Salt Conditions", MABS, vol. 5, No. 5 (2013) pp. 795-800.
H. Chen et al., "Monoclonal Antibody and Antibody Drug Conjugate Separation by Polymer Based Reversed Phase Chromatography", PEGS 2014, Protein and Antibody Engineering Summit (2014) XP55184437.
Feng et al: "Current therapeutic antibody production and process optimization", Bioprocessing, Sep. 1, 2005, pp. 23-30, XP002519952.
Kuczewski et al: "Development of a polishing step using a hydrophobic interaction membrane adsorber with a PER.C6-derived recombinant antibody", Biotechnology and Bioengineering, vol. 105, No. 2, Feb. 1, 2010, pp. 296-305, XP002585901.
Notification of reasons for refusal in corresponding JP patent application No. 2016-555750 dated Jan. 18, 2019(paes 1-4).

* cited by examiner

*Primary Examiner* — Daniel E Kolker
*Assistant Examiner* — James L Rogers
(74) *Attorney, Agent, or Firm* — Millen White Zelano & Branigan, PC

(57) ABSTRACT

The present invention refers to a method for the separation of host cell proteins (HCPs), antibody fragments and low molecular weight substances from solutions containing antibodies.

19 Claims, 11 Drawing Sheets

ROBUST ANTIBODY PURIFICATION

Figure 1A:
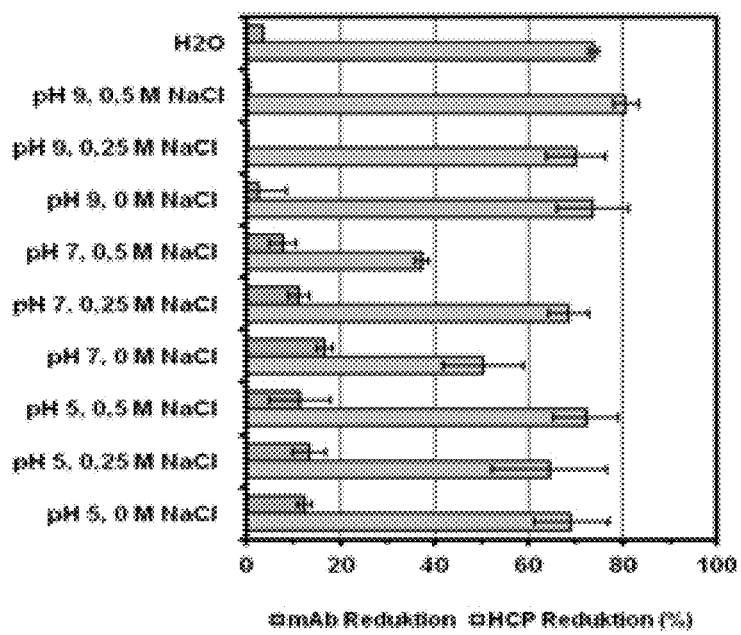

The present invention refers to a method for the separation of host cell proteins (HCPs), antibody fragments and low molecular weight substances from solutions containing antibodies.

STATE OF THE ART

Protein A and Purification of Monoclonal Antibodies

Since antibodies (mAbs) are used for pharmaceutical applications, they are required in exceptionally high purities [A. Jungbauer, G. Carta, in: Protein Chromatography, Process Development and Scale-Up; WILEY-VCH Verlag, Weinheim (Germany) 2010].

Protein A is initially a 56 kDa surface protein originally found in the cell wall of the bacterium *Staphylococcus aureus*. It is encoded by the spa gene and its regulation is controlled by DNA topology, cellular osmolarity, and a two-component system called ArlS-ArlR. It has found use in biochemical research because of its ability to bind immunoglobulins. It is originally composed of five homologous Ig-binding domains that fold into a three-helix bundle. Each domain is able to bind proteins from many mammalian species, most notably IgGs. It binds the heavy chain within the Fc region of most immunoglobulins and also within the Fab region in the case of the human VH3 family. Through these interactions in serum, where IgG molecules are bound in the wrong orientation (in relation to normal antibody function), the bacteria disrupts opsonization and phagocytosis.

In general mammalian cell cultures are employed to manufacture the majority of therapeutic monoclonal antibodies (mAbs) currently on the market. Production of these drug antibodies typically starts in a bioreactor that contains a suspension of Chinese Hamster Ovary (CHO) cells which secrete the antibody into the extracellular fluid. The resulting antibodies are then subjected to a series of processes including clarification, filtration, and purification that removes cells, cell debris, host cell proteins (HCP), lipids, DNA, viruses, bacteria, antibody aggregates, etc. This series of processes is often referred to as a downstream process (DSP).

Most commonly employed DSP includes one or two bind-elute chromatography purification steps followed by one or two flow-through polishing steps. Typical downstream purification processes employ packed columns filled with porous bead-based chromatography media or membrane-based devices. These unit operations are employed in series and each are targeted towards clearing a particulate impurity in either a flow-through polishing or a bind/elute capture mode. One of the primary objectives of the polishing media is to reduce the concentration of impurities (e.g. HCP down to <10 ppm in reference to mAb concentration).

In summary, a typical antibody purification process includes an initial Protein A affinity capture step followed by one or more ion exchange polishing steps, the purpose of which is to reduce the level of one or more critical impurities such as, e.g., host cell protein (HCP), antibody fragments and other low molecular weight substances. Antibody fragments are especially hard to separate from antibodies since they have similar properties, especially FC containing fragments. The latter are generally not separated using Protein A chromatography.

In general, further antibody purification steps (e.g. CEX, AEX) are performed after Protein A capture step at certain conditions to remove the remaining impurities. This requires numerous adjustments of antibody holding solution prior those purification steps (e.g. pH adjustment, conductivity adjustment). Furthermore, these pH and conductivity shifts, stress the molecule of interest, and antibody related impurities are generated (e.g. antibody aggregates, antibody fragments).

Recently, there has been a noticeable trend in the industry to try and reduce the number of purification steps maintaining the product quality attributes. Also, use of techniques for obtaining a higher expression titer using bioreactors is a rising trend in the industry. The combination of these two trends has resulted in loading more of the product onto a column, thereby resulting in increased burden of fairly expensive chromatography media as well as lower product purity, both of which are undesirable.

In order to improve the selectivity of the chromatographic purification of desired proteinaceous products like antibodies or special protein fragments, various chromatographic materials have been developed in parallel to the alteration of purification methods. Especially specific derivatizations of surfaces of separation materials should lead to a more selective separation of undesired impurities from the desired products in clarified cell culture media. But these special and complex surface derivatizations make the production of these chromatography materials a lot more expensive than commercially available products, so that their use in industrial scale purifications is less attractive.

Other developments in the field of chromatography materials were drawn to separation materials based on organic substrates, because commercially available materials, based on silica materials, are generally affected in a basic milieu and lose stability, particularly during regeneration.

Stationary phases based on organic polymers can be operated over a wide range of pH conditions. Thus, the polymeric resins may be cleaned aggressively under high pH conditions. But current polymeric stationary phases are somewhat compressible at the medium to high pressure conditions used in high-performance biomolecule separations.

Conventional macroporous copolymers produced from the suspension polymerization of divinylbenzene(DVB)-containing mixtures in the presence of a non-solvent represent polymers having a wide range of pore size distributions and surface areas. Such polymer beads are for example disclosed in U.S. Pat. No. 4,686,269. These polymer beads are prepared from vinyl-aromatic monomers, having average particle diameters from 0.5 to 50 μm. But they are not rigid under high pressure conditions commonly used in production scale chromatography columns. Rigidity of polymer beads used in chromatography is essential because it provides together with the porous polymer stationary phase the necessary pressure and flow characteristics during separation.

Object

The problem to be solved is the need for robust and reliable antibody purification step, effectively applicable in a wide range of conditions in a flow through mode, where the level of critical impurities, such as HCP and antibody fragments is reduced.

SUMMARY OF THE INVENTION

The present invention relates to a method for the separation of host cell proteins (HCPs), antibody fragments and low molecular weight substances from solutions containing antibodies, wherein a solution containing antibodies is contacted with a hydrophobic chromatography material for a suitable time period whereby the antibodies stay predominantly in solution and HCPs, antibody fragments and low molecular weight substances are adsorbed by the hydrophobic chromatography material.

In detail, the hydrophobic chromatography material is particulate and it is made of cross-linked vinylbenzene, ethylstyrtene, poly(ethyl)styrene-divinylbenzene, or of poly(ethyl)styrene-divinylbenzene ethyleneglycol-dimethylacrylate resin. Preferably the resin is composed of cross-linked polymer composed of styrene and divinylbenzene in a ratio 98:2 up to 10:90% by weight. In modified form, the particulate material consists of polystyrene, which is cross-linked with copolymer of divinylbenzene and ethylengly-coldi-methacrylate in a ratio of 98:2 up to 10:90% by weight.

In order to carry out the removal and separation of host cell proteins (HCPs), antibody fragments and low molecular weight substances from the desired antibody an aqueous clarified cell culture solution, having a pH value in the range of 2-11, preferably in a range of 5-9 and a conductivity in the range of 1-150 mS/cm, preferably in the range of 2-50 mS/cm, is contacte with a hydrophobic chromatography material. Preferably the aqueous solution is passed through at a flow rate in the range of 150-1000 cm/min, preferably in the range of 300-900 cm/min. In a particularly preferred embodiment the separation of host cell proteins (HCPs), antibody fragments and low molecular weight substances is processed after the Protein A affinity binding step. If required, the purification sequence includes a treatment with ion exchange resin.

Usually the separation is processed using particulate, hydrophobic chromatographic separation materials having mean particle diameters in the range of 10 μm to 600 μm, preferably in the range of 20 μm to 150 μm, most preferably in the range of 20 μm to 63 μm. Suitable hydrophobic porous polymer beads of this size have preferable pore sizes in the range of 4-500 nm, more preferable in the range of 10-30 nm, most preferred in the range of 13 nm to 25 nm.

As indicated above, the purification sequence may include at least one treatment with an ion exchange resin, which preferably is specific for the separation of Protein A. A combined treatment with such ion exchange resins and a treatment with porous hydrophobic polymer beads advantageously results in a depletion of up to <10 ng HCP and a simultaneous removal of leached Protein A. Particularly good cleaning effects are obtained in this case if the hydrophobic polymer particles consist of cross-linked vinylbenzene, poly(ethyl)styrene-divinylbenzene, or of poly(ethyl) styrene-divinylbenzene ethyleneglycol-dimethylacrylate resin.

The object of the present invention is, in particular, the use of hydrophobic chromatographic separation materials having pore sizes in the range of 4 nm to 500 nm, preferably in the range of 10 nm-30 nm, most preferably in the range of 13 nm to 25 nm for the separation of host cell proteins (HCPs), antibody fragments and low molecular weight substances from solutions containing antibodies. The used hydrophobic chromatographic separation materials of the present invention are preferably made of cross-linked vinylbenzene, crosslinked ethylstyrene, polystyrene/polyethylstyrene-divinylbenzene, or of polystyrene/polyethylstyrene-divinylbenzene ethyleneglycol-dimethylacrylate resin. In an especially preferred embodiment the used hydrophobic, rigid polymer beads described herein, have mean particle diameters in the range of 10 μm to 600 μm, preferably in the range of 20 μm to 150 μm, most preferably in the range of 20 μm to 63 μm, and pore sizes in the range of 4 nm to 500 nm, preferably in the range of 10 nm-30 nm, most preferably in the range of 13 nm to 25 nm.

DETAILED DESCRIPTION OF THE INVENTION

In various experiments described herein it was found that porous hydrophobic interaction materials such as porous poly(di)vinyl aromatic beads are useful for large scale antibody purification from cell culture solutions. These purification steps can be done either upstream or downstream of a capture chromatography step in order to reduce the level of one or more impurities present in a sample (e.g., a clarified cell culture solution) containing a protein of interest.

For this purpose, the clarified cell culture solution is brought into contact with the hydrophobic interaction material, for example into contact with porous hydrophobic polystyrene beads, and incubated for a certain period of time in order to selectively reduce the level of low molecular weight substances. By this procedure, it is possible to selectively reduce unwanted antibody fragments and HCPs from the culture solution containing the antibody of interest. Said hydrophobic interaction material is especially suitable to be subjected to post Protein A capture antibody solutions and for selectively reducing the level of low molecular weight substances (e.g. antibody fragments, HCPs) by contacting a clarified cell culture solution with the material for a suitable period of time. For carrying out this purification process the hydrophobic interaction material (e.g., polystyrene beads) is incorporated into one or several chromatography column(s) or other devices, such as filter housings and the like. These packed columns are then used for protein purification processes in a flow-through mode, whereby low molecular weight substances, such as antibody fragments and HCPs of the culture solution interact with the hydrophobic, porous interaction material during the flow through the column and the level of low molecular weight substances (e.g. antibody fragments, HCP) is reduced. In this case, good purification results are obtained, when the flow velocity is adjusted to be in the range of 150 cm/min-1000 cm/min, and especially between 300-900 cm/min.

Further, in experiments described herein, it was found, that good purification results are achievable if the pH of the clarified culture broth is adjusted to be in a range between 2 to 11, and preferably in the range 3 to 9.

At the same time, it has proven to be advantageous if the conductivity of the solution is in the range of 1 mS/cm-50 mS/cm, and especially in the range between 2-50 mS/cm.

As demonstrated by the experiments herein, it was found to be especially surprising that high purities of the clarified cell culture media can be achieved by the use of hydrophobic interaction materials in form of small porous polymer beads. In some embodiments this material may mainly consists of polystyrene or polyethylstyrene and can be crosslinked by a mixture of hydrophobic and hydrophilic monomers, for example divinylbenzene (DVB) and ethylene glycol dimethacrylate (EGDMA).

The porous polymer beads are typically produced by suspension polymerization. They may be produced in a process, which is for example similar to that disclosed in U.S. Pat. No. 4,382,124 and where porosity is introduced into the copolymer beads by suspension polymerization in the presence of a porogen (also known as "phase extender" or precipitant"), which is a solvent for the monomer but a nonsolvent for the polymer. Conventional porous polymers, such as those prepared according to U.S. Pat. No. 4,382,124 typically encompass the use of a wide range of porogen types, porogen concentrations relative to the monomer phase, monomer types, crosslinking monomer types, crosslinker levels, polymerization initiators and initiator concentrations. The present invention, however, is based on the unexpected finding that when the ratio of hydrophobic monomers is in a special range, these polymer beads are especially suitable and effective in purification of antibodies from cell culture liquids.

While not wishing to be bound by theory, it is believed that in the case of the present invention the increased capacity for target molecules is primarily achieved when the polymer matrix is altered by increasing the contained shares of hydrophobic molecules in the polymer. This alteration was done considering the balance of the polymer building monomers and of the amount of porogens and of crosslinker levels which altogether influence the parameters of porosity, rigidity and binding capacity of target molecules.

Surprisingly, a significantly improved separation of HCPs can be achieved by these selected open porous hydrophobic polymer beads. The porous structure enables rapid diffusion of molecules into and out the polymer matrix, and because of the porosity of the polymer beads a large surface area is available for the interaction with unwanted proteins and impurities contained in the cell culture medium. Thus, these materials are very effective in separating a biomolecule in a stationary phase. Most modern, commercial polymeric Reverse Phase Chromatography stationary phases appear to be designed around these criteria, and are used under lower pressure conditions, however, at higher pressure conditions (typically in the range of 10 to 100 bar) these materials are compressible. Fortunately, polymer beads according to the present invention have increased rigidity, and at the same time have a high porosity, thereby providing a high capacity for intraparticle diffusion.

The hydrophobic porous polymer beads used in the present invention are useful for the removal of host cell proteins (HCPs), antibody fragments and low molecular weight substances from solutions containing monoclonal antibodies by contacting the solution with the polymer beads in a liquid chromatography column having a diameter ranging from 1 to 100 cm, preferably in the range of 5 to 50 cm, where the column is operated at pressures up to 100 bar, and preferably at pressure ranging from 0.2 to 80 bar. Typically, preparative scale columns are in the range of 10 to 50 cm and are operated at pressures in the range of 0.2 to 80 bar.

The porous polymer beads according to the present invention are typically spherical copolymer beads having an average particle size diameter up to 200 μm, which is the typical size for polymer beads useful for the separation and purification of biomolecules via high performance reverse phase liquid chromatography (such as in columns ranging from 1 to 100 cm in diameter).

In general, porous separation materials have been found particularly effective when they have average particle size diameters ($d_{50}$) in the range of 10-600 μm, preferably in the range of 20-150 μm, whereas such materials having average particle sizes in the range of 20-63 μm have shown to be particularly effective.

Such hydrophobic separation materials, preferably polystyrene beads, appear to be suitable for the desired separation effect, having pore size in the range of 4-500 nm. Purification experiments have shown that hydrophobic interaction materials, having average pore sizes between 10-30 nm, lead to desireable separation results. These desirable separation results can be further improved when spherical hydrophobic polymer beads are used, which are made from a suitable material and an average pore size in the range between 13-25 nm. Suitable porous polymer beads of the present invention preferably possess surface areas (BET) in the range of 300 to 1000 $m^2/g$ (square meters per gram), more preferably in the range of 450 to 850 $m^2/g$, and most preferably in the range of 500 to 800 $m^2/g$.

Suitable monounsaturated vinylaromatic monomers that may be used in the preparation of the porous polymer beads described herein include, but are not limited to, styrene, C1-C4-alkyl-substituted styrenes, vinylnaphthalene and vinylanthracene. Preferably the monounsaturated vinylaromatic monomer is selected from one or more of styrene and C1-C4-alkyl-substituted styrenes. Included in the group of suitable C1-C4-alkylsubstituted styrenes are ethylvinylbenzenes, vinyltoluenes, dieethylstyrenes, ethylmethylstyrenes and dimethylstyrenes. It is understood, that any of the various positional isomers of each of the aforementioned vinylaromatic monomers is suitable.

This means, porous polymer beads suitable in the present invention particularly may be prepared using one or more monomer(s) selected from the group consisting of vinylbenzene (styrene), ethylstyrene, divinylbenzene, trivinylbenzene, divinyltoluene, divinylnaphthalene, divinylanthracene, divinylxylene and any structural isomer of these monomers.

Preferably the porous polymers are prepared using copolymers of vinylbenzene (styrene) and divinylbenzene or ethylstyrene and divinylbenzene. In a preferred embodiment of the invention the applied crosslinked porous polymer beads comprise styrene/and divinylbenzene in a weight ratio to one another of from 98:2 to 10:90%.

Optionally aliphatic unsaturated monomers, for example (meth)acrylic acids and alkyl esters of (meth)acrylic acids may also be used in addition to the vinylaromatic monomer for the preparation of said hydrophobic, porous polymer beads described herein. These aliphatic unsaturated monomers may be used as crosslinking agents in the preparation of the desired polymer beads.

Suitable aliphatic crosslinking monomers are selected from the group consisting of ethyleneglycol diacrylate, ethyleneglycol dimethacrylate, trimethylolpropane triacrylate, trimethylolpropane trimethacrylate, dieethyleneglycol divinyl ether and trivinylcyclohexane, and which may be used for the preparation of crosslinked hydrophobic porous polymer beads according to the present invention. The aliphatic monomers can be used alone or in combination with polyvinylaromatic monomers mentioned above as crosslinking monomers.

In both variants, ethyleneglycol dimethacrylate, glycidyl methacrylate, and diethyleneglycol divinyl ether are especially suitable for the preparation of porous beads. Preferably these aliphatic crosslinking monomers are used in combination with polyvinylaromatic crosslinking monomers. Under these conditions, the aliphatic monomers typically are comprised in an amount ranging from 0 to 50% and preferably in an amount ranging from 0 to 30%, based on the total monomer weight used to form the rigid and porous polymer beads.

In the inventive use of porous polymer particles described herein superior separation results are achieved using porous polymer beads consisting of polystyrene, which is crosslinked with a copolymer of divinylbenzene or a derivative thereof and a monomer selected from the group consisting of ethyleneglycol dimethacrylate, and diethyleneglycol divinyl ether and wherein the ratio of polystyrene and crosslinking copolymer is in a range of 98:2 up to 10:90% by weight. In a preferred embodiment porous particles consisting of poly (ethyl)styrene are used, which are crosslinked with copolymer of divinylbentzene and ethyleneglycol methacrylate in a ratio of 98:2 up to 14:86% by weight. In this connection, it has been found that for the separation of host cell proteins (HCPs), antibody fragments and low molecular weight substances from solutions containing antibodies porous beads are better suited, in which(di)vinylaromatic monomers are contained in an amount of more than 50% by weight. Thus porous beads, consisting of polymer of monovinylaromatics, which is crosslinked with copolymer of divinylbenzene and ethyleneglycol methacrylate in a ratio of about 10:90 to 98:2% by weight are preferred. More preferred are such porous beads wherein the ratio is about 14:86 by weight.

Preferred hydrophobic porous polymers are selected from one or more of vinylbenzene (styrene) copolymer, ethylvinylbenzene (ethylstyrene) copolymer, divinylbenzene copolymer, crosslinked polystyrene-divinylbenzene copolymer, crosslinked polystyrene ethyleneglycol-dimethacrylate, crosslinked polydivinylbenzene ethyleneglycol-dimethacrylate. Most preferred are crosslinked poly(ethyl)styrene-divinylbenzene copolymer and poly(ethyl)styrene crosslinked with copolymer of divinylbenzene and ethyleneglycol-dimethacrylate.

Porogens useful for preparing the porous polymers include hydrophobic porogens, such as ($C_7$-$C_{10}$) aromatic hydrocarbons, and ($C_6$-$C_{12}$) saturated hydrocarbons and hydrophilic porogens, such as ($C_4$-$C_{10}$) alkanols and polyalkylene glycols. Thus suitable porogens can, for example, be selected from the group consisting of toluene, ethylbenzene, ortho-xylene, meta-xylene, para-xylene. It is understood that, any of the various positional isomers of any of the aforementioned hydrocarbons is suitable. Preferably, the aromatic hydrocarbon is toluene or xylene or a mixture of xylenes or a mixture of toluene and xylene. Furthermore as indicated above, saturated hydrocarbons canalso be used as porogens. Suitable examples include, but are not limited to are for example hexane, heptanes or isooctane. The preferred saturated hydrocarbon in this case of the present invention is isooctane. Suitable alkanols include, but are not limited to isobutyl alcohol, tert-amyl alcohol, n-amyl alcohol, isoamyl alcohol, methyl isobutyl carbinol, (4-methyl-2-pentanol), hexanols and octanols. Preferably a porogen mixture comprises a hydrophilic porogen selected from one or more ($C_5$-$C_8$)alkanol and a hydrophobic porogen selected from one or more ($C_7$-$C_{10}$) aromatic hydrocarbon.

Typically the porogen is added to the polymerization suspension in excess, usually in a total amount of 100 to 170%, preferably from 115-150 and more preferably from 120 to 140%, based on weight of the monomers. In addition, the porogens used to prepare the polymers according to the present invention are mixed with a solvent system, which comprises at least a hydrophobic solvent and optionally a less hydrophobic solvent ("hydrophilic" solvent) and which both support the building of porous beads. It is self-explanatory that the less hydrophobic (or "hydrophilic" as stated above) solvent has at least some limited water solubility, for example, ranging from 0.5 to 5% whereas the hydrophobic solvent shows a water solubility of 10 to 100 ppm or less.

Generally, the ratio of porogen with low hydrophobicity (i.e., "hydrophilic porogen") to the hydrophobic porogen is in the range of 0.7:1 up to 3:1, preferably in the range of 0.8:1 up to 2.5:1, most preferably from 0.9:1 to 2.4:1.

Polymerization initiators useful in preparing polymers suitable in the present invention are well known to one of ordinary skill in the art and include monomer soluble initiators like peroxides, hydroperoxides, and related initiators. These initiators are commercially available. Also useful are azo initiators such as azodiisobutyronitrile, azodiisobutyramide and the like. Depending on the nature of the initiator the use levels are in ranges of 0.5 to 10% based on the total weight of the comprising vinyl monomers.

Furthermore, dispersants or suspending agents useful for preparing the porous polymer beads may be customary surfactants, which are ionic and may contain hydrophobic alkyl chains containing 1 to 24 carbon atoms. Another commercially available group of dispersants which is suitable in the suspension polymerization are nonionic surfactants, which are based on epoxidized hydroxyalkylcellulose derivatives. Typically these additives are used at levels of about 0.01 up to 4% based on the total weight of the aqueous phase.

If suitable, other dispersants may be used and can be applied together with those surfactants and dispersants. For example, polymeric dispersants including celluloses, polyvinyl pyrrolidones, polyvinyl alcohols, starches and the like may be used in mixtures with other surfactants or dispersants used herein. But most preferred is the addition of ionic surfactants, which can be easily removed from the prepared polymer beads by rinsing with water.

For the preparation of the porous hydrophobic polymer beads disclosed herein, a continuous aqueous phase solution containing suspension aids is prepared and then this solution is mixed with a monomer mixture containing the polyvinylaromatic monomer, free-radical initiator and for example 1 to 1.7 parts of (mixed) porogen (hydrophobic and hydrophilic porogen) per one part monomer mixture. The monomer/porogen combinations then polymerized at elevated temperature (typically at 40 to 100° C., for example for 1 to about 15 hours) and the porogens are subsequently removed from the resulting polymer beads, for example by distillation or solvent washing. The resulting porous polymer beads are then isolated by conventional means, like dewatering and drying.

Optionally the preparation of the polymer beads may include a treatment to cleanse the polymer surface of residues of dispersants and suspending agents used during the polymerization. This treatment may include an enzyme treatment as disclosed in the patent literature (JP 61-141704 or JP 57-98504 or EP 1 179 732 B1).

Prepared polymer beads are especially suitable in packed columns, because of their porosity and mechanical strength. Advantageously, these porous and rigid polymer beads are useful for the separation of host cell proteins (HCPs), antibody fragments and low molecular weight substances from solutions containing antibodies by contacting the solution with these polymer beads in liquid chromatography columns even at elevated pressures. These beads are especially suitable for high performance separations and purifications of biomolecules at high throughput rates without pressure buildup because of prolonged use.

Porous polymer beads as used in the present invention are characterized by selected porosities and pore size distributions, which may be determined by inverse size-exclusion chromatography (iSEC). The polymer beads suitable in the present invention typically have a porosity ε in the range of 0.4 to 1.0 and preferably in the range of 0.45 to 0.75. These beads possess surface area ranging from 300 to 100 $m^2$/g [BET], more preferably from 450 to 850 $m^2$/g, and most preferably in the very narrow range of 500 to 800 $m^2$/g.

The polymer beads as disclosed here are unexpectedly well suited for the separation of host cell proteins (HCPs), antibody fragments and low molecular weight substances from solutions containing monoclonal antibodies. Because of their chemical nature and their nano porous structure these materials are especially suitable for hydrophobic interaction with low molecular weight proteins and can be incorporated into chromatography column based protein purification processes in a flow-through mode. The properties of the these porous polymer beads and the type of process control result in a reduction of the burden of chromatography columns, and consequently the life span of chromatography columns is increased, while the levels of critical impurities, such as HCP and antibody fragments is reduced. Advantageously the applied polystyrene beads need not to be derivatized and, therefore are much more cost effective than commonly used chromatography gels in this purification step. The separation materials described herein are fairly inexpensive and can be regenerated, thereby reducing the overall costs of antibody purification platform and beyond.

Further, surprisingly hydrophobic materials described herein can be used either upstream or downstream of a capture chromatography step to reduce the level of one or more impurities. In some embodiments according to the claimed methods, a sample is contacted with a hydrophobic material before the Protein A affinity chromatography step. In general, the Protein A affinity chromatography step is used before contacting a sample with a hydrophobic material.

Additionally, the application of hydrophobic material is not limited to the given examples, since it is based on size exclusion mechanisms and hydrophobic adsorption of low molecular weight substances, especially compounds of molecular mass <70 kDa. This results in a selective removal of monoclonal antibody related molecules, such as antibody fragments or HCP.

Furthermore, the present invention provides a chromatography based antibody purification step, wherein the chromatography material described herein can be regenerated and is applicable in wide operation window (e.g. pH 3-11; conductivity 1 mS/cm-50 mS/cm, operational velocity 150 cm/min-1000 cm/min). In particular, the resistance of the porous polymer beads at low and high pH values is of great advantage here because a satisfactory regeneration is possible and these materials have a considerably longer life span.

As already indicated above, the removal of low molecular weight substances, especially compounds of molecular mass <70 kDa, from clarified cell culture broths using the hydrophobic porous polymer beads described herein may be performed both at industrial and as well as micro-scale, as the selected separation materials are stable against pressure and are not prone to deformation at high pressures. The user is free in the manner of carrying out the chromatographic purification. It is self-explanatory that depending on the nature of the applied cell culture and of the low molecular weight proteins, one or the other composition of the porous polymer particles may be advantageous for the purification step. Here the expert has the choice between porous polymers made from pure (vinyl) alkyl aromatics or those that are crosslinked by suitable acrylates. In this case, the most suitable polymers beads can be readily indentified by one of ordinary skill in the art.

But these materials are not limited to be used for the removal of low molecular weight substances, especially compounds of molecular mass <70 kDa like antibody fragments or HCP. Surprisingly, it was found that Protein A, which is not separated in previous purification steps or which is washed out, can easily be separated from cell culture media using the porous hydrophobic polymer beads according to the present invention. Surprisingly, the separation of Protein A from cell culture media can be effected independently from the pH value of the medium using the porous polymer beads. In experiments it can be shown that for example PS-DVB-EGDMA resin is able to adsorb Protein A in pH 4.00 and pH 8.00 solutions under static binding conditions.

In case of combined treatment with commercially available ion exchange resin specific for the separation of Protein A and with porous hydrophobic polymer beads and where devices are connected one after another in a sequence, for example columns packed with ion exchange resins, for example packed with Eshmuno®CPX followed by Eshmuno®Q followed by PS-DVB-EGDMA, a depletion of up to <10 ng HCP is easily reached, including removal of leached Protein A.

The present description enables one of ordinary skill in the art to practice the present invention comprehensively. Even without further comments, it is therefore assumed that a person of ordinary skill in the art will be able to utilise the above description in the broadest scope.

If anything is unclear, it is understood that the publications and patent literature cited should be consulted. Accordingly, these documents are regarded as part of the disclosure content of the present description.

For better understanding and in order to illustrate the invention, examples are described below which are within the scope of protection of the present invention. These examples also serve to illustrate possible variants.

Furthermore, it goes without saying to one of ordinary skill in the art that, both in the examples given and also in the remainder of the description, the component amounts present in the compositions always only add up to 100% by weight or mol %, based on the composition as a whole, and cannot exceed this percentage, even if higher values could arise from the percent ranges indicated. Unless indicated otherwise, % data are therefore % by weight or mol %, with the exception of ratios, which are shown in volume data.

As used throughout the specification, the following terms shall have the following meanings, unless the context clearly indicates otherwise:

The term "alkyl(meth)acrylate" refers to either corresponding acrylate or methacrylate ester; similarly, the term "(meth)acrylic" refers to either acrylic or methacrylic acid and the corresponding derivatives, such as esters or amides. As indicated above, all percentages referred to will be expressed in weight percent (%), based on total weight of polymer or composition (solution) involved, unless specified otherwise. The term "copolymer" refers to polymer compositions containing units of two or more different monomers, including positional isomers.

The following abbreviations are used herein:
g=grams,
ppm=parts per million by weight/volume,
m=meter,
cm=centimeter,
mm=millimeter,
μm=micrometer (micron)=$10^{-6}$ m,
nm=nanometer=$10^{-9}$ m,
ml=milliliter, L=Liter. Unless otherwise specified, ranges listed are to be read as inclusive and combinable.
The temperatures given in the examples and the description as well as in the claims are always degrees centigrade (° C.).
Methods:
Particle Charateristics:
Characterization of particles is known in the art and is described by: I. C. Edmundson, Particle-size analysis. H. S.

Bean, A. H. Beckett and J. E. Caries (eds) in: Advances in Pharmaceutical Sciences vol. 2, Academic Press, London 1967, 95-174.

The particle size distribution and the average diameter may be measured by laser diffractometry using Mastersizer 2000E (Malvern Instruments Ltd., UK) or by a laser light blocking technique (Accusizer™ model 770, Particle Sizing Systems, Santa Barbara, Calif., USA).

The shape and surface characteristics (porosity) of the microspheres may be established by scanning electron microscopy (SEM) analysis.

The pore size is determined by methods which are known in the art. Macropores may be determined using mercury porosimetry. In this case experiments for analyzing pore sizes are done following the protocol of the used mercury porosimetry analyzer (e.g. AutoPore IV 9500, Micromeritics, USA). It is also possible to estimate the pore dimensions from scanning electron micrographs (SEM) where the diameter and surface features of the polymer microspheres are observed after drying by scanning electron microscope (SEM) (JSM-6700F. JEOL, Japan). Microspheres are re-suspended in distilled water and the dispersion is dropped on a piece of aluminum foil and dried at ambient atmosphere. The sample is placed on a metal stub with double-sided conductive adhesive tape and is coated with a thin gold film under reduced pressure below 5 Pa with a JFC-1600 fine coater (JEOL, Japan).

The pore size of mesopores and their specific surface area can also determined using nitrogen adsorption/desorption measurements (BET-method), which are performed by following standard protocols. This latter method may also be used for determining the BET surface area.

HCP ELISA Test

Purified proteins always contain small amounts of contaminating proteins from the expression organism, referred to as host cell proteins (HCPs). These Host Cell Proteins (HCP's) in biological products are process-related impurities that must be identified and evaluated qualitatively and quantitatively. To quantify the purification effectivity of the separation method disclosed herein is an ELISA (enzyme-linked immunosorbent assay) test system, which is used. ELISA test systems are process-specific for the detection of HCPs from a specific bacterium or from specific cultured cell lines (e.g. Chinese Hamster Ovary (CHO) cell cultures).

The principle of, for example, a CHO HCP ELISA kit is based on the binding of CHO proteins in samples to two antibodies, one immobilized on the microwells, and the other conjugated to horseradish peroxidase (HRP). After incubation and a washing step, chromogenic substrate (TMB) is added and color is developed by the enzymatic reaction of HRP on the substrate, which is directly proportional to the amount of antigen present in the sample. Stopping Solution is added to terminate the reaction, and absorbance at 450 nm is then measured using an ELISA microwell reader. The concentration of CHO proteins in samples and control is calculated from a standard curve of CHO HCPs.

Another method for quantification of separated HCPs done by SDS-PAGE, followed by band analysis via BioDoc gel analysis software.

The principle of the SOS-PAGE analysis consists of SDS polyacrylamide gel electrophoresis (SDS-PAGE) and involves the separation of proteins based on their size. By heating the sample under denaturing and reducing conditions, proteins become unfolded and coated with SOS detergent molecules, acquiring a high net negative charge that is proportional to the length of the polypeptide chain. When loaded onto a gel matrix and placed in an electric field, the negatively charged protein molecules migrate towards the positively charged electrode and are separated by a molecular sieving effect. After visualization by a protein-specific staining technique, the size of a protein can be estimated by comparison of its migration distance with that of a standard of known molecular weight. It is also possible to blot the separated proteins onto a positively charged membrane and to probe with protein-specific antibodies in a procedure termed western blotting.

The documentation and subsequent analysis of the separated proteins can be made via BioDocAnalyze system, a digital scientific grade camera and included software for analysis of gels and blots. This system is commercially available.

FIGURE LIST

FIG. 1a: mAb03 reduction and HCP reduction (%) in various antibody post Protein A capture pools after treatment at different conditions.

Figure 1B:
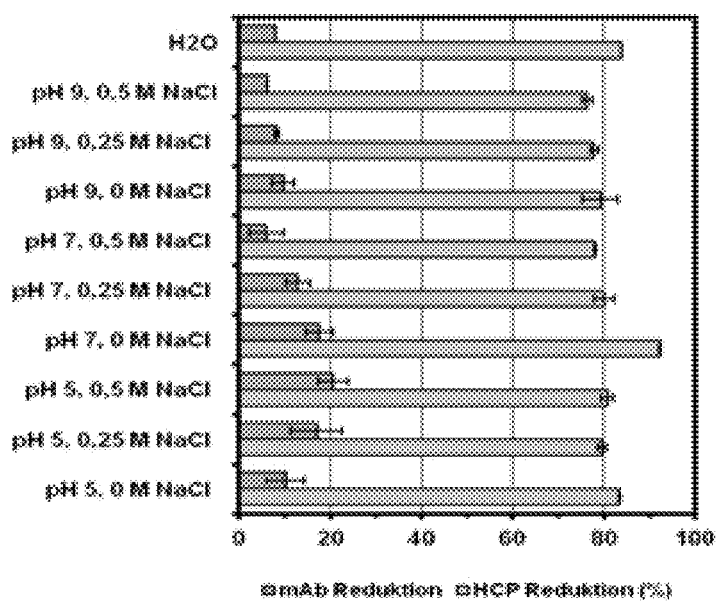
Figure 1C:
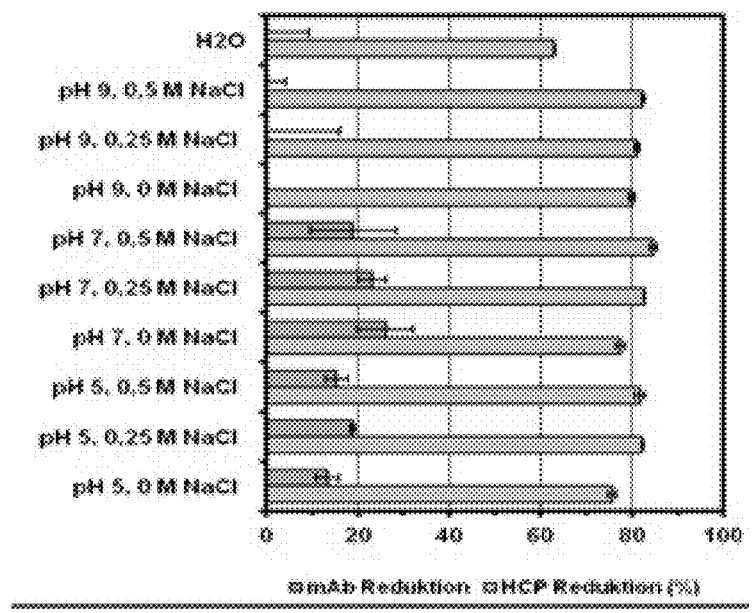
Figure 1D:
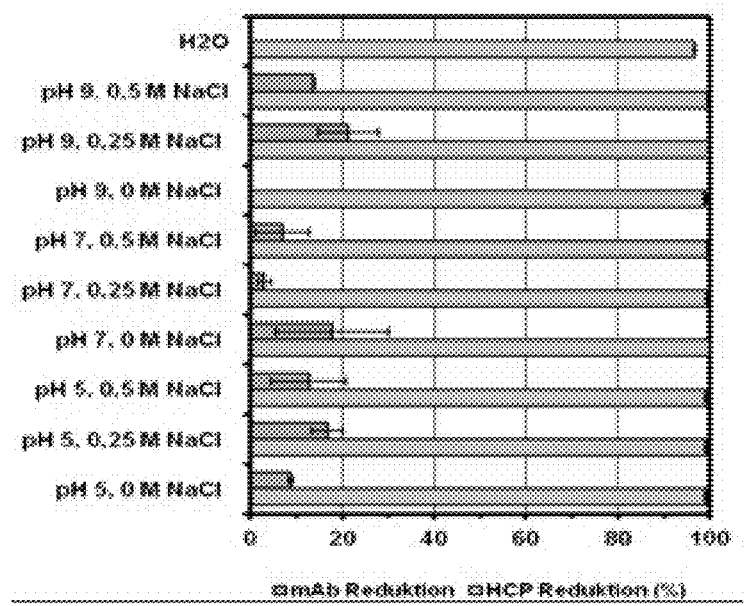
Figure 2A:
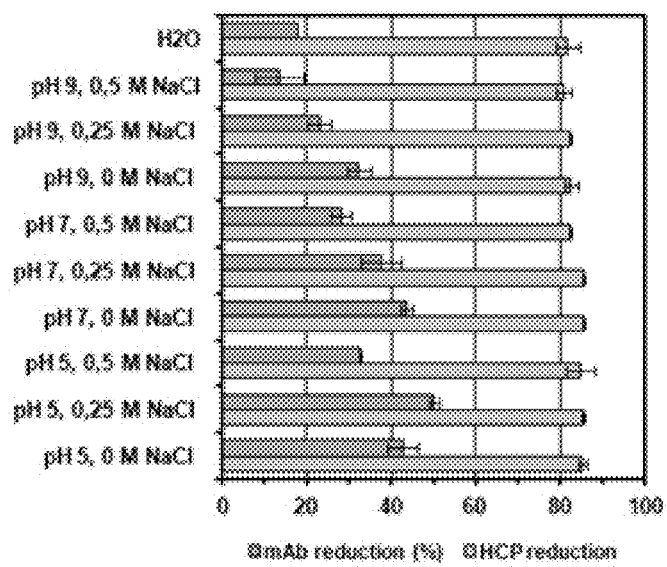

FIG. 1b: mAb05 reduction and HCP reduction (%) in various antibody post Protein A capture pools after treatment at different conditions FIG. 1c: mAb07 reduction and HCP reduction (%) in various antibody post Protein A capture pools after treatment at different conditions FIG. 1d: mAb08 reduction and HCP reduction (%) in various antibody post Protein A capture pools after treatment at different conditions FIG. 2a: mAb05 reduction and HCP reduction (%) after treatment at different conditions with porous PS-DVB particulate material having 31.4 nm diameter average pores.

Figure 2B:
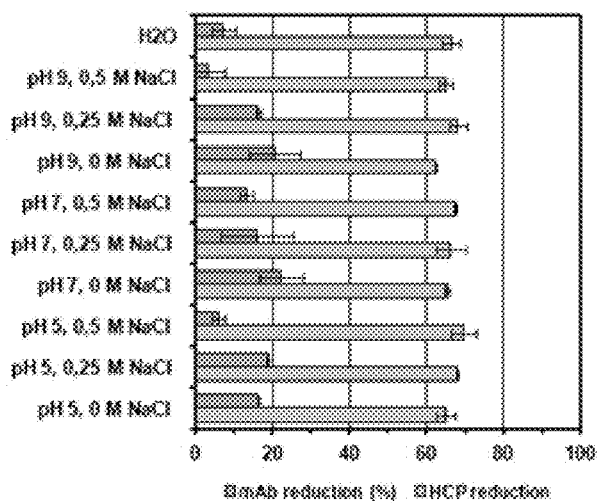

FIG. 2b: mAb05 reduction and HCP reduction (%) after treatment at different conditions with PS-DVB particulate material having 20.4 nm diameter average pores.

Figure 2C:
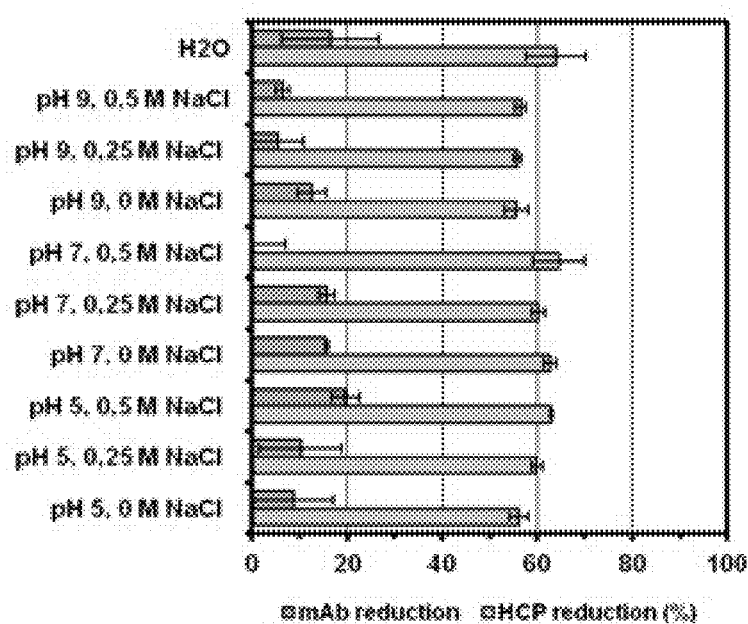

FIG. 2c: mAb05 reduction and HCP reduction (%) after treatment at different conditions with PS-DVB particulate material having 15.8 nm diameter average pores.

Figure 3:
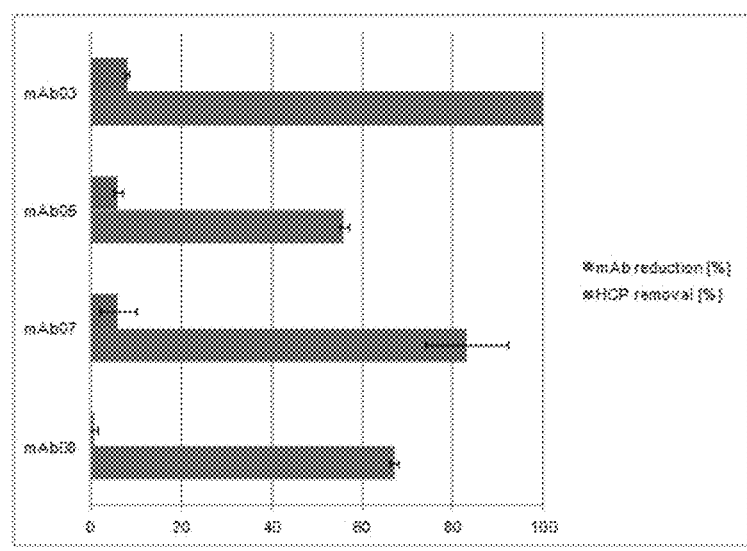

FIG. 3: mAb reduction and HCP reduction (%) after treatment with PS-DVB particulate material having 15.8 nm diameter average pores.

Figure 4:
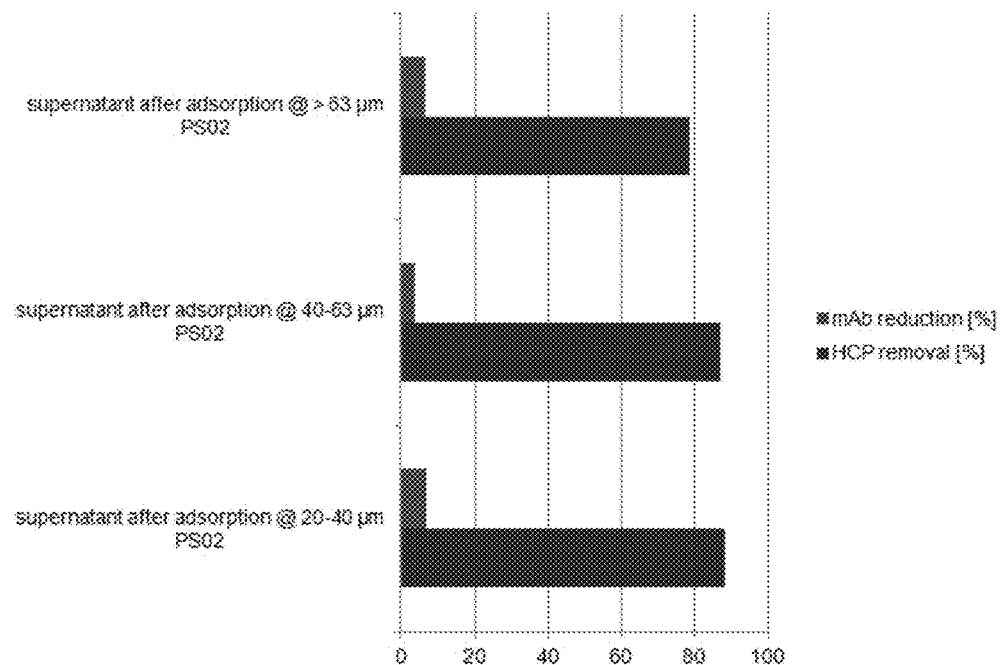

FIG. 4: mAb reduction and HCP reduction (%) after treatment with PS-DVB particulate material having 15.8 nm diameter average pores and classified to different particles sizes, ranging from >63 μm (top line), to 40-63 μm (middle line) and to 20-40 μm (bottom line).

Figure 5:
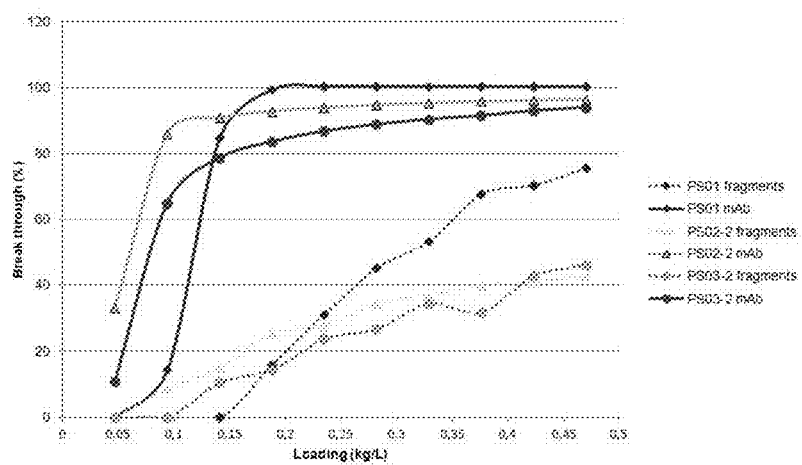

FIG. 5: mAb03 levels and FC containing fragment break through levels at different loadings for PS-DVB (PS01)—average pore size 31.4 nm, for PS-DVB (PS02)—average pore size 20.4 nm and PS-DVB (PS03)—average pore size 15.8 nm particulate materials.

Figure 6:
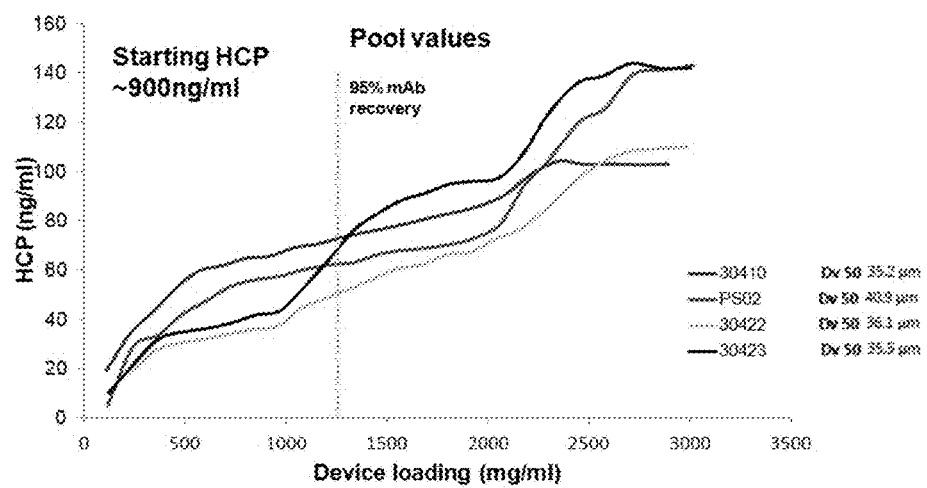

FIG. 6: mAb03 levels and HCP break through levels at different loadings for PS-DVB-EGDMA particulate material, where 30422 ($d_{50}$-36.1 μm) and PS02 ($d_{50}$-40.9 μm) materials consists of poly(ethyl)styrene (m), crosslinked with divinylbenzene copolymers, 30410 ($d_{50}$-35.2 μm) material consists of poly(ethyl)styrene (m), crosslinked with divinylbenzene (70%) and ethylene glycol dimethylacrylate (30%) copolymers and 30423 ($d_{50}$-35.5 μm) consists of poly(ethyl)styrene (m), crosslinked with divinylbenzene (50%) and ethylene glycol dimethylacrylate (50%) copolymers.

Figure 7A:
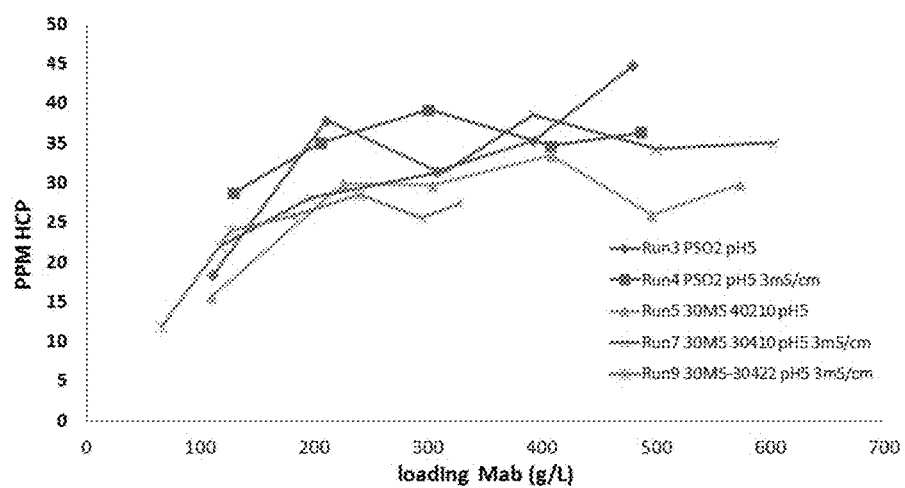

FIG. 7a: mAb06 HCP break through levels at different loadings for PS-DVB-EGDMA particulate material, where 30422 ($d_{50}$-36.1 μm) and PS02 ($d_{50}$-40.9 μm) materials consists of poly(ethyl)styrene (m), crosslinked with divinylbenzene copolymers, 30410 ($d_{50}$-35.2 μm) material consists of poly(ethyl)styrene (m), crosslinked with divinylbenzene (70%) and ethylene glycol dimethylacrylate (30%) copolymers. Run 3 and Run 5 performed with mAb06 post Protein A pool (pH 5.0, conductivity-1.4 mS/cm) and run 4, run 7 and run 9 were performed with mAb06 post Protein A pool, where NaCl was added to increase the pool conductivity to 3 mS/cm.

Figure 7B:
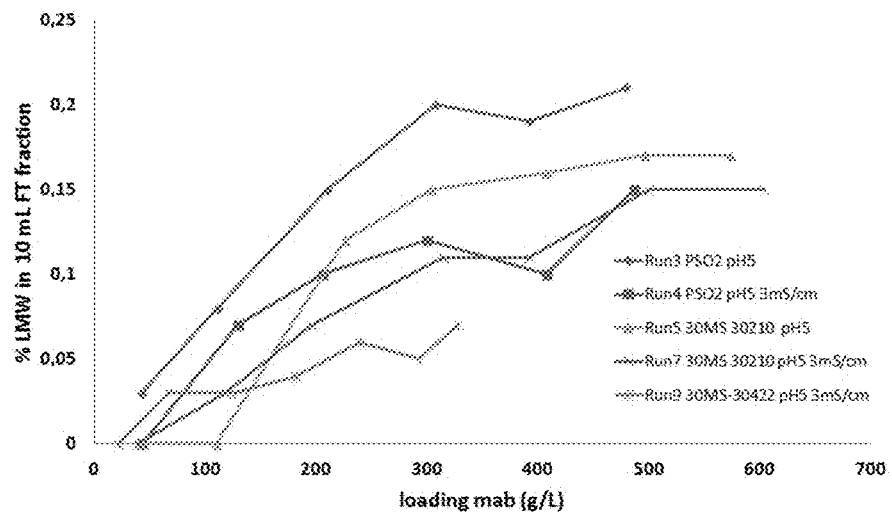

FIG. 7b: mAb06 LMW (%) break through levels at different loadings for PS-DVB-EGDMA particulate material, where 30422 ($d_{50}$-36.1 μm) and PS02 ($d_{50}$-40.9 μm) materials consists of poly(ethyl)styrene (m), crosslinked with divinylbenzene copolymers, 30410 ($d_{50}$-35.2 μm) material consists of poly(ethyl)styrene (m), crosslinked with divinylbenzene (70%) and ethylene glycol dimethylacrylate (30%) copolymers. Run 3 and Run 5 performed with mAb06 post Protein A pool (pH 5.0, conductivity-1.4 mS/cm) and run 4, run 7 and run 9 were performed with mAb06 post Protein A pool, where NaCl was added to increase the pool conductivity to 3 mS/cm.

Figure 7C:
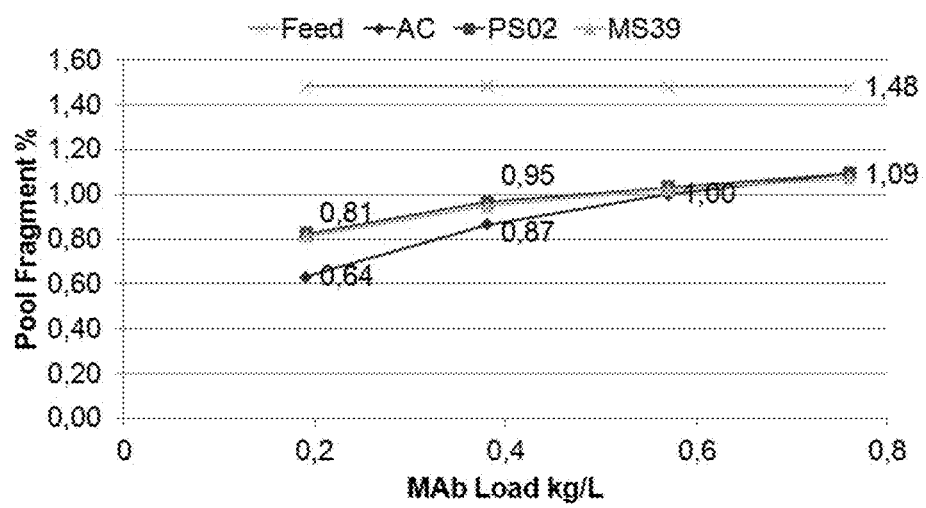

FIG. 7c: mAb05 LMW (%) break through levels at different loadings for PS-DVB-EGDMA particulate material, where PS02 ($d_{50}$-40.9 μm) materials consists of poly(ethyl)styrene (m), crosslinked with divinylbenzene copolymers, MS39 ($d_{50}$-35.2 μm) material consists of poly(ethyl)styrene (m), crosslinked with divinylbenzene (70%) and ethylene glycol dimethylacrylate (30%) copolymers and AC is natural activated carbon (Nuchar HD).

Figure 7D:
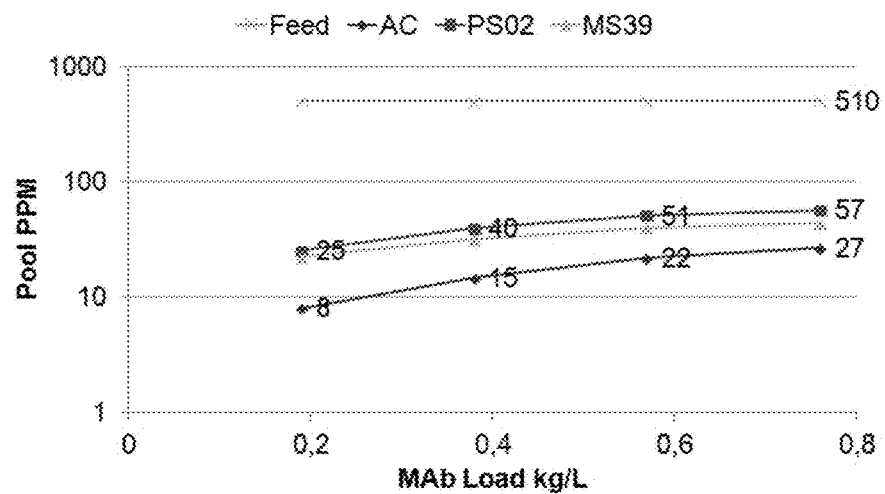

FIG. 7d: mAb05 HCP break through levels at different loadings for PS-DVB-EGDMA particulate material, where PS02 ($d_{50}$-40.9 μm) materials consists of poly(ethyl)styrene (m), crosslinked with divinylbenzene copolymers, MS39 ($d_{50}$-35.2 μm) material consists of poly(ethyl)styrene (m), crosslinked with divinylbenzene (70%) and ethylene glycol dimethylacrylate (30%) copolymers and AC is natural activated carbon (Nuchar HD).

Figure 8:
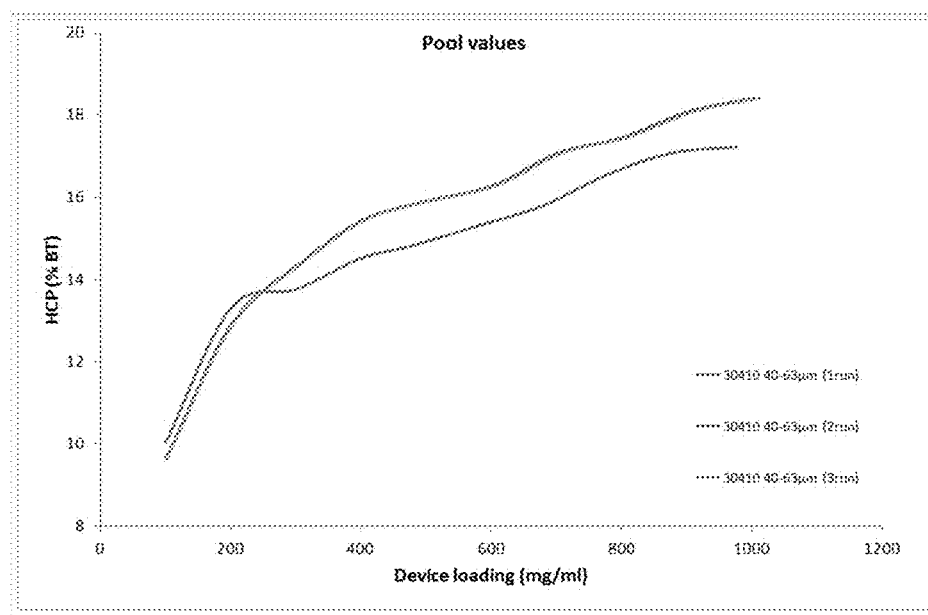

FIG. 8: mAb03 HCP break through levels at different loadings for PS-DVB-EGDMA particulate material, where 30410 material consists of poly(ethyl)styrene (m), crosslinked with divinylbenzene (70%) and ethylene glycol dimethylacrylate (30%) copolymers. Runs 1-3 represent sequential runs after column cleaning and reequilibration.

Figure 9:
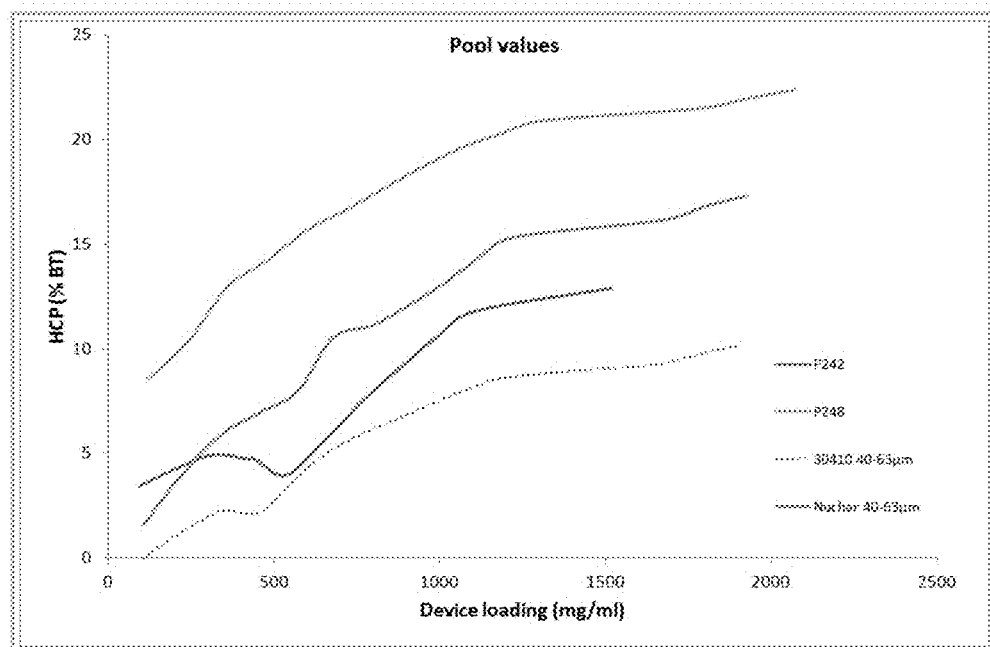

FIG. 9: mAb03 HCP break through levels at different loadings for PS-DVB-EGDMA particulate material, where 30410 material consists of poly(ethyl)styrene (m), crosslinked with divinylbenzene (70%) and ethylene glycol dimethylacrylate (30%) copolymers. P242 is competitor hydrophobic material, P248 is competitor hydrophobic material and Nuchar HD is activated carbon material, which is sized to 40-63 μm.

Figure 10A:
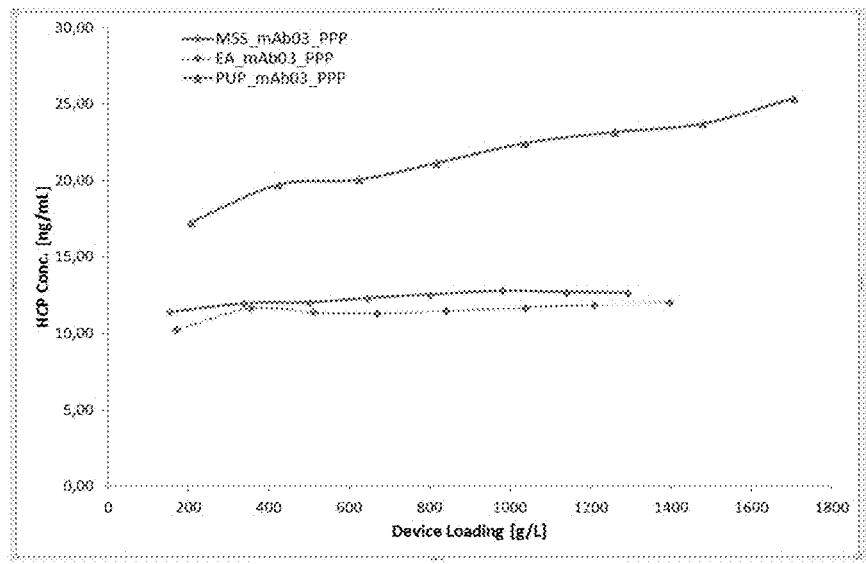

FIG. 10a: HCP levels in various mAb03 post Protein A (e.g. Prosep Ultra Plus (PUP), Mab Select Sure, Eshmuno A) pools after different loadings on PS-DVB-EGDMA particulate material, where this material consists of poly(ethyl)styrene (m), crosslinked with divinylbenzene (70%) and ethylene glycol dimethacrylate (30%) copolymers.

Figure 10B:
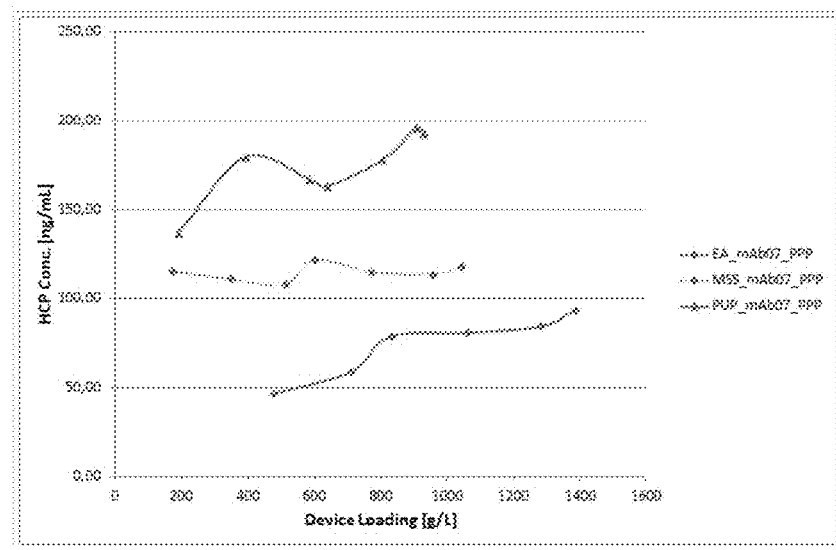

FIG. 10b: HCP levels in various mAb07 Protein A (e.g. PUP, MAB Select Sure Eshmuno A) pools after different loadings on PS-DVB-EGDMA particulate material, where this material consists of poly(ethyl)styrene (m), crosslinked with divinylbenzene (70%) and ethylene glycol dimethylacrylate (30%) copolymers.

Figure 11:
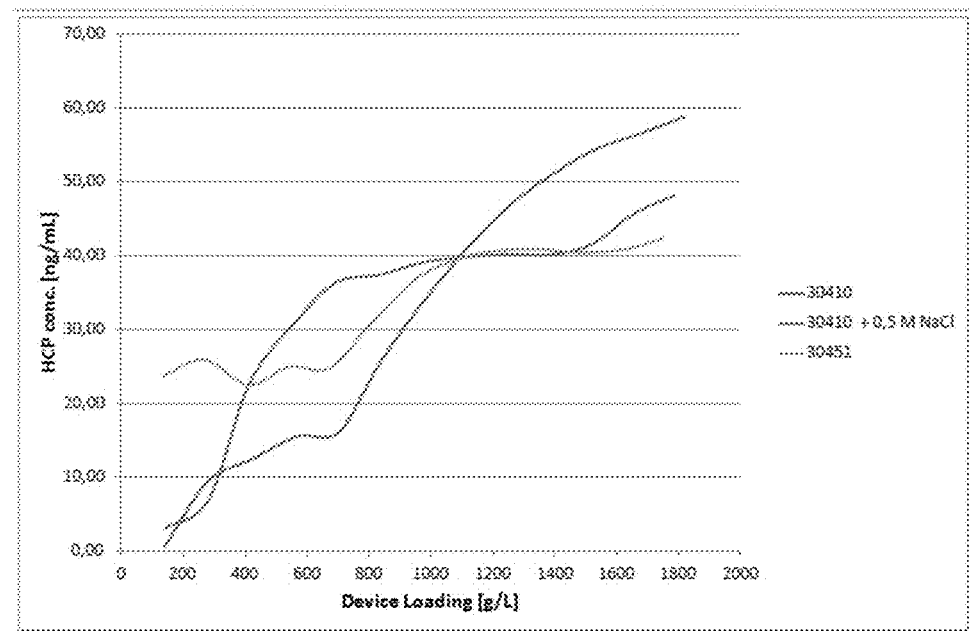

FIG. 11: mAb03 HCP break through levels at different loadings for PS-DVB-EGDMA particulate material, where in one experiment NaCl was added to 0.5M concentration. 30451 materials consists of poly(ethyl)styrene (m), crosslinked with divinylbenzene copolymers, 30410 material consists of poly(ethyl)styrene (m), crosslinked with divinylbenzene (70%) and ethylene glycol dimethylacrylate (30%) copolymers.

Figure 12:
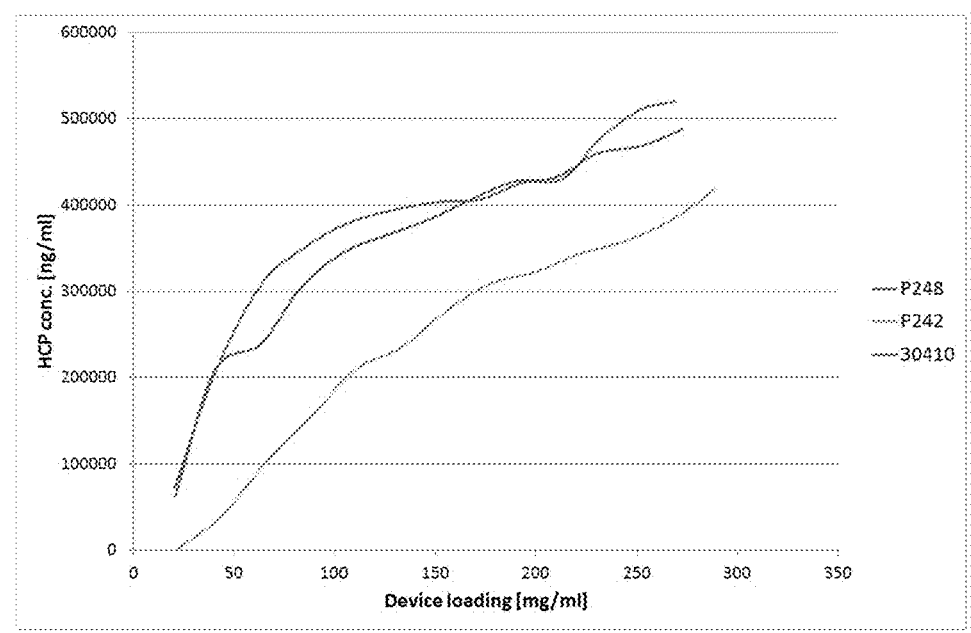

FIG. 12: mAb03 HCP break through levels operated at 900 cm/h for different loadings for PS-DVB-EGDMA particulate material, where 30410 material consists of poly(ethyl)styrene (m), crosslinked with divinylbenzene (70%) and ethylene glycol dimethylacrylate (30%) copolymers. P242 is competitor hydrophobic material, P248 is competitor hydrophobic material as well.

Figure 13:
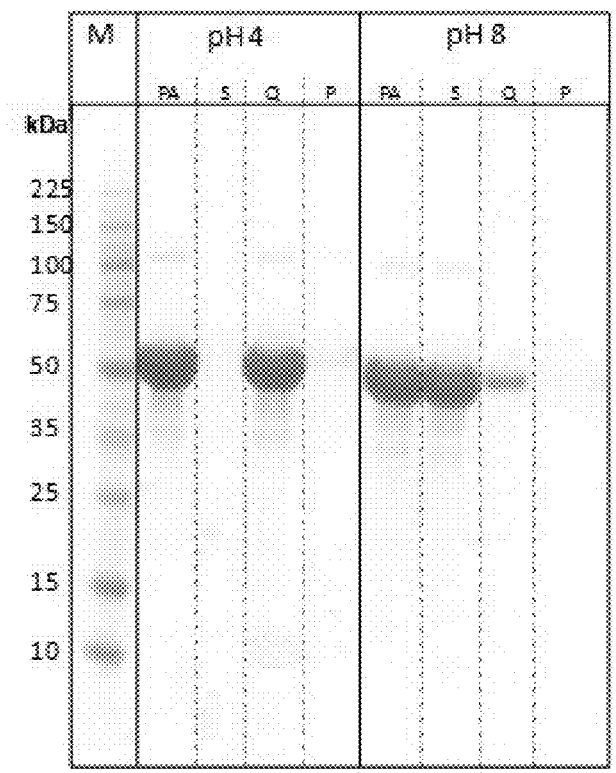

FIG. 13: Reduced SDS PAGE analysis of Protein A adsorption on DVB-EGDMA, Eshmuno® S, and Eshmuno® Q resins

EXAMPLES

Base Beads

Synthesis of Polystyrene Based Material (Such as P353, P374 and P375)

25.6 g Polyvinylalcohol and 0.38 g SDS are dissolved in 614.2 g water to form the water phase for the following suspension polymerization. The organic phase is formed by a homogenous solution of 19.94 g ethylvinylbenzene, 75 g divinylbenzene, 41.57 g ethylene glycol dimethacrylate, 90.24 g toluene, 90.24 g 2-ethyl-1-hexanole and 0.96 g AIBN. The organic phase is added to the water phase in a reactor vessel and the two phases are emulsified at 25° C. with a stirrer at 480 rpm to achieve the anticipated particle size distribution. After 60 min 640 g water are added and the reaction mixture is heated up to 72° C. For two hours the temperature is kept at 72° C. and then increased to 82° C. The mixture is polymerized at 82° C. for additional two hours. Following polymerization the suspension is filtered on a filter funnel and the particles are washed with 1.5 liter water of 60° C., followed by 5 liter methanol at 60° C., 5 liter of toluene and 2 liter of methanol at 40° C. The final product is dried in a vacuum oven for 24 hours at 50° C. and 50 mbar. The yield regarding dry mass is quantitative. Depending from the anticipated particle size distribution the final product is classified by sieving according to procedures which are state of the art.

Example 1

In this experiment, different materials are evaluated for their ability to remove impurities from a post Protein A capture pools. Two hydrophobic materials:
a) particulate material consisting of polyethyl)styrene (m), crosslinked with divinylbenzene copolymers (PS-DVB) and
b) particulate material consisting of polystyrene (m), crosslinked with divinylbenzene copolymers and ethylene glycol dimethylacrylate (PS-DVB-EGDMA) copolymers, are tested for impurity removal in static mode. Phosphate buffer saline (PBS, 10 mM phosphate, pH 7.4) is used as an equilibrium and wash buffer for the tested materials prior to subjecting them to a post Protein A capture pools. Samples are subjected to two different post Protein A capture pools overnight under vigorous shaking and under a set of loadings corresponding to an antibody loading (weight ratio) per volume of particulate material. Those loadings are 0.5, 1 and 2 kg/L. After overnight incubation the particulate material is filtered out and the samples are analyzed using size exclusion chromatography, HCP ELISA and HPLC Prot A methods to gather the performance data. The result of this experiment shows that both the particulate materials used in this experiment adsorb HCP and antibody fragments (see Table 1, 2).

TABLE 1

Static fragment removal for multiple antibodies

| Antibody | Material | Starting amount of fragment (%) | 2 kg/L loading | 1 kg/L loading | 0.5 kg/L loading |
|---|---|---|---|---|---|
| mAb04 | PS-DVB | 1.97 | 1.41 | 0.88 | 0.00 |
| mAb04 | PS-DVB-EGDMA | 1.99 | 1.62 | 1.18 | 0.72 |
| mAb05 | PS-DVB | 0.31 | 0.12 | 0.03 | 0.00 |
| mAb05 | PS-DVB-EGDMA | 0.31 | 0.15 | 0.10 | 0.00 |

TABLE 2

Static host cell protein removal from multiple antibodies

| Antibody | Material | 2 kg/L loading (LRV removal) | 1 kg/L loading (LRV removal) | 0.5 kg/L loading (LRV removal) |
|---|---|---|---|---|
| mAb04 | PS-DVB | 0.61 | 0.96 | 1.24 |
| mAb04 | PS-DVB-EGDMA | 0.45 | 0.91 | 1.29 |
| mAb05 | PS-DVB | 1.71 | 2.15 | 2.21 |
| mAb05 | PS-DVB-EGDMA | 1.63 | 1.89 | 2.26 |

The antibody yields in all of those experiments were greater than 80%.

Example 2

In this experiment, different materials are evaluated for their ability to remove added antibody fragments from post Protein A capture pools.

Hydrophobic Materials:

a) particulate material consisting of poly(ethyl)styrene (m), crosslinked with divinylbenzene copolymers (PS-DVB) and b) particulate material consisting of poly(ethyl)styrene (m), crosslinked with divinylbenzene copolymers and ethylene glycol dimethylacrylate (PS-DVB-EGDMA) copolymers, are examined for their ability to remove impurities in static mode.

Phosphate buffer saline (PBS, 10 mM phosphate, pH 7.4) is used as an equilibrium and wash buffer for the tested materials prior to subjecting them to model post Protein A capture pools, which are enriched with papain digested antibody solution. Samples are subjected to generated post Protein A capture pools overnight under vigorous shaking and under a set of loadings corresponding to an antibody loading (weight ratio) per volume of particulate material. The loadings are 0.5 and 1 kg/L. After overnight incubation, the particulate material is filtered out and the samples are analyzed using size exclusion chromatography and HPLC Prot A methods to gather the performance data. It is noted that both particulate materials used adsorb added antibody fragments (see Table 3 below).

TABLE 3

Static fragment removal of added antibody fragments

| Antibody | Material | 1 kg/L loading (LRV removal) | 0.5 kg/L loading (LRV removal) |
|---|---|---|---|
| mAb08 | PS-DVB | 0.22 | 0.48 |
| mAb08 | PS-DVB-EGDMA | 0.9 | 0.21 |

In all experiments, the antibody yields are higher than 80%.

Example 3

In this experiment, particulate material, consisting of poly(ethy)styrene (m) crosslinked with divinylbenzene copolymers (PS-DVB), is evaluated for its ability to remove HCP from various antibody post Protein A capture pools, where post Protein A pools are adjusted to a wide range of pH and conductivity conditions. Measurements are made in duplicates, mixing 25 µl particulate material and 1000 µl PPP (phosvitin phosphopeptides; diluted 1:4 in buffers of different pH and NaCl conc.) and incubated for 30 minutes. HCP reduction is quantified via ELISA assays, whereas mAb reduction is quantified via SDS-PAGE and subsequent band analysis is performed via BioDoc gel analysis software (see FIG. 1a-d).

FIG. 1a: mAb03 reduction and HCP reduction (%) after treatment at different conditions FIG. 1b: mAb05 reduction and HCP reduction (%) after treatment at different conditions FIG. 1c: mAb07 reduction and HCP reduction (%) after treatment at different conditions FIG. 1d: mAb08 reduction and HCP reduction (%) after treatment at different conditions Example 4

In this experiment, particulate materials consisting of poly(ethyl)styrene (m), crosslinked with divinylbenzene copolymers (PS-DVB) having different average pore sizes (estimated by inverse SEC and PSS software) are evaluated for their ability to remove HCP from clarified cell culture pool, which has been adjusted to a wide range of pH and conductivity conditions. Measurements are made in duplicates, mixing 25 µl particulate material and 1000 µl PPP (diluted 1:4 in buffers of different pH and NaCl conc.) and incubated for 30 minutes. HCP reduction is quantified via ELISA assays, whereas mAb reduction is quantified via SDS-PAGE and subsequent band analysis is performed via BioDoc gel analysis software (see FIG. 2a-c):

FIG. 2a: mAb05 reduction and HCP reduction (%) after treatment at different conditions with PS-DVB particulate material having an average pore size of 31.4 nm in diameter.

FIG. 2b: mAb05 reduction and HCP reduction (%) after treatment at different conditions with PS-DVB particulate material having an average pore size of 20.4 nm in diameter.

FIG. 2c: mAb05 reduction and HCP reduction (%) after treatment at different conditions with PS-DVB particulate material having an average pore size of 15.8 nm in diameter Example 5

In this experiment, particulate material consisting of poly(ethyl)styrene (m), crosslinked with divinylbenzene copolymers (PS-DVB) having an average pore size of 15.8 nm (estimated by inverse SEC and PSS software) is evaluated for its ability to remove HCP from clarified cell culture pool. Measurements are made in duplicates, mixing 25 µl particulate material and 1000 µl PPP (diluted 1:4 in 50 mM TRIS pH 9 0.5 M NaCl) and incubated for 30 minutes. HCP reduction is quantified via ELISA assays, whereas mAb reduction is quantified via SDS-PAGE and subsequent—band analysis is performed via BioDoc gel analysis software (see FIG. 3):

FIG. 3: mAb reduction and HCP reduction (%) after treatment with PS-DVB particulate material having average pore sizes of 15.8 nm in diameter.

Example 6

In this experiment, particulate material consisting of poly(ethyl)styrene (m), crosslinked with divinylbenzene copolymers (PS-DVB), having an average pore size of 15.8 nm (estimated by inverse SEC and PSS software) and classified (wet sieving) to different particulate material size ranges, is evaluated for its ability to remove HCP from post Protein A capture pools. Measurements are made in duplicates, mixing 25 µl particulate material and 1000 µl PPP (diluted 1:4 in 50 mM TRIS pH 9 0.5 M NaCl) and incubated for 30 minutes. HCP reduction is quantified via ELISA assays, whereas mAb reduction is quantified via SDS-PAGE and subsequent band analysis is performed via BioDoc gel analysis software (see FIG. 4):

FIG. 4: mAb reduction and HCP reduction (%) after treatment with PS-DVB particulate material having 15.8 nm diameter average pores and classified to different particles sizes, ranging from >63 µm (top line), to 40-63 µm (middle line) and to 20-40 µm (bottom line).

Example 7

In this experiment, particulate materials consisting of poly(ethyl)styrene (m) crosslinked with divinylbenzene copolymers (PS-DVB) having different average pore size (estimated by inverse SEC and PSS software) are evaluated for their ability to remove introduced heavy chain (FC) containing antibody fragments after papain digestion and Prot A affinity purification from a post Protein A antibody pool, where the known amount of digested and purified FC containing antibody fragments is spiked in antibody post Protein A pool. Measurements are performed in dynamic mode, of packing the particulate material in the chromatographic column and charging it with prepared feed at 300 cm/h after equilibration using 50 mM acetate buffer at pH 5.0. Fragment levels are quantified via SEC-HPLC (see FIG. 5):

FIG. 5: mAb03 levels and FC containing fragment break through levels at different loadings for PS-DVB (PS01)—average pore size 31.4 nm, for PS-DVB (PS02)—average pore size 20.4 nm and PS-DVB (PS03)—average pore size 15.8 nm particulate materials.

Example 8

In this experiment, particulate materials consisting of poly(ethyl)styrene (m) crosslinked with divinylbenzene (PS-DVB) and ethylene glycol dimethylacrylate (PS-DVB-EGDMA) copolymers in various ratios are evaluated for their ability to remove HCP from a post Protein A antibody pool. Measurements are performed in dynamic mode, of packing the particulate material in the chromatographic column and charging it with mAb03 post Protein A feed (pH 5.0 LF~3 mS/cm) @ 350 cm/h after equilibration with 50 mM Acetate buffer pH 5.0, LF ~2 mS/cm for at >20 CV. The starting HCP concentration is 900 ng/ml and mAb concentration 8.4 mg/ml. All materials sized to 20-40 µm particle size and average particle size distribution estimated with Accusizer. Antibody levels were quantified via SEC-HPLC and HCP amount via ELISA measurements (see FIG. 6):

FIG. 6: mAb03 levels and HCP break through levels at different loadings for PS-DVB-EGDMA particulate material, where 30422 ($d_{50}$-36.1 µm) and PS02 ($d_{50}$-40.9 µm) materials consists of poly(ethyl)styrene (m) crosslinked with divinylbenzene copolymers, 30410 ($d_{50}$-35.2 µm) material consists of poly(ethyl)styrene (m) crosslinked with divinylbenzene (70%) and ethylene glycol dimethylacrylate (30%) copolymers and 30423 (d50-35.5 µm) consists of poly(ethyl) styrene (m) crosslinked with divinylbenzene (50%) and ethylene glycol dimethylacrylate (50%) copolymers.

Example 9

In this experiment, particulate materials consisting of poly(ethyl)styrene (m) crosslinked with divinylbenzene (PS-DVB) and ethylene glycol dimethylacrylate (PS-DVB-EGDMA) copolymers in various ratios are evaluated for their ability to remove HCP and low molecular weight substances (e.g. antibody fragments) from various post Protein A antibody pools. Measurements are performed in dynamic mode, of packing the particulate material in the chromatographic column and charging it with antibody post Protein A feed (pH 5.0) @ 300 cm/h after equilibration with 50 mM Acetate buffer pH 5.0, LF ~2 mS/cm for at >20 CV. All materials sized to 20-40 µm particle size and average particle size distribution estimated with Accusizer. Antibody levels are quantified via SEC-HPLC and HCP amount via ELISA measurements (see FIG. 7a-d):

FIG. 7a: mAb06 HCP break through levels at different loadings for PS-DVB-EGDMA particulate material, are 30422 (d50-36.1 µm) and PS02 (d50-40.9 µm) materials consists of poly(ethyl)styrene (m) crosslinked with divinylbenzene copolymers, 30410 (d50-35.2 µm) material consists of poly(ethyl)styrene (m) crosslinked with divinylbenzene (70%) and ethylene glycol dimethylacrylate (30%) copolymers. Run 3 and Run 5 are performed with mAb06 post Protein A pool (pH 5.0, conductivity-1.4 mS/cm) and run 4, run 7 and run 9 are performed with mAb06 post Protein A pool, where NaCl is added to increase the pool conductivity to 3 mS/cm.

FIG. 7b: mAb06 LMW (%) break through levels at different loadings for PS-DVB-EGDMA particulate material, where 30422 ($d_{50}$-36.1 µm) and PS02 ($d_{50}$-40.9 µm) materials consists of poly(ethyl)styrene (m) crosslinked with divinylbenzene copolymers, 30410 ($d_{50}$-35.2 µm) material consists of poly(ethyl)styrene (m) crosslinked with divinylbenzene (70%) and ethylene glycol dimethylacrylate (30%) copolymers. Run 3 and Run 5 performed with mAb06 post Protein A pool (pH 5.0, conductivity-1.4 mS/cm) and run 4, run 7 and run 9 are performed with mAb06 post Protein A pool, where NaCl is added to increase the pool conductivity to 3 mS/cm.

FIG. 7c: mAb05 LMW (%) break through levels at different loadings for PS-DVB-EGDMA particulate material, where PS02 ($d_{50}$-40.9 µm) materials consists of poly(ethyl)styrene (m) crosslinked with divinylbenzene copolymers, MS39 ($d_{50}$-35.2 µm) material consists of poly(ethyl) styrene (m), crosslinked with divinylbenzene (70%) and ethylene glycol dimethylacrylate (30%) copolymers and AC is natural activated carbon (Nuchar HD).

FIG. 7d: mAb05 HCP break through levels at different loadings for PS-DVB-EGDMA particulate material, where PS02 ($d_{50}$-40.9 μm) materials consists of poly(ethyl)styrene (m) crosslinked with divinylbenzene copolymers, MS39 ($d_{50}$-35.2 μm) material consists of poly(ethyl)styrene (m) crosslinked with divinylbenzene (70%) and ethylene glycol dimethylacrylate (30%) copolymers and AC is natural activated carbon (Nuchar HD).

Example 10

In this experiment, particulate materials consisting of poly(ethyl)styrene (m) crosslinked with divinylbenzene (PS-DVB) (70%) and ethylene glycol dimethylacrylate (PS-DVB-EGDMA) (30%) copolymers are evaluated for their ability to remove HCP from various post Protein A antibody pools and reuse the particulate material after cleaning. Measurements are performed in dynamic mode, of packing the particulate material in the chromatographic column and charging it with post Protein A antibody feed (pH 5.0) @ 300 cm/h after equilibration with 50 mM Acetate buffer pH 5.0, LF ~2 mS/cm for at >20 CV. The materials sized to 40-63 μm particle size and average particle size distribution estimated with Accusizer. After use, the column is eluted with 60% DPG solution for 20 CV and re-equilibrated with 50 mM Acetate buffer pH 5.0, LF ~2 mS/cm for at >20 CV. Antibody levels are quantified via SEC-HPLC and HCP amount via ELISA measurements (see FIG. 8):

FIG. 8: mAb03 HCP break through levels at different loadings for PS-DVB-EGDMA particulate material, where 30410 material consists of poly(ethyl)styrene (m) crosslinked with divinylbenzene (70%) and ethylene glycol dimethylacrylate (30%) copolymers. Run 1-3 represent sequential runs after column cleaning and reequilibration.

Example 11

In this experiment, particulate material consisting of poly (ethyl)styrene (m), crosslinked with divinylbenzene (PS-DVB) (70%) and ethylene glycol dimethylacrylate (PS-DVB-EGDMA) (30%) copolymers is evaluated in comparison to commercially available hydrophobic material for their ability to remove HCP from various post Protein A antibody pools. Measurements are performed in dynamic mode, of packing the particulate material in the chromatographic column and charging it with post Protein A antibody feed (pH 5.0) @ 600 cm/h after equilibration with 50 mM Acetate buffer pH 5.0, LF ~2 mS/cm for at >20 CV. Antibody levels are quantified via SEC-HPLC an d HCP amount via Elisa measurements (see FIG. 9):

FIG. 9: mAb03 HCP break through levels at different loadings for PS-DVB-EGDMA particulate material, where 30410 material consists of poly(ethyl)styrene (m) crosslinked with divinylbenzene (70%) and ethylene glycol dimethylacrylate (30%) copolymers. P242 is competitor hydrophobic material, P248 is competitor hydrophobic material and Nuchar HD is activated carbon material, which was sized to 40-63 μm.

Example 12

The Application of Different Types of Activated Carbon or Hydrophobic Resins for the Removal of Monoclonal Antibody Fragments from a Solution of a Monoclonal Antibody Under Static Conditions This representative example demonstrates that monoclonal antibody fragments can be selectively removed from a solution of a monoclonal antibody by static treatment with different types of activated carbon and different type of hydrophobic resins.

Solutions of MAB08 are prepared with approximately 1.7% of monoclonal antibody fragments and then are treated with one of three different types of activated carbon or two different types hydrophobic resin under static conditions, as described below.

MAB08 stock solutions are prepared by treatment of the purified monoclonal antibody with papain enzyme to digest them into fragments. After digestion the enzyme is inactivated by adding a solution of 0.3 M iodoacetate. The digested monoclonal antibody solutions are dialyzed into water with dialysis tubing (Standard RC Dialysis Trial Kits, Spectra/Por 1-3, 3.5K MWCO, 54 mm FLAT WIDTH, serial number: 132725, Spectrum Laboratories, Inc., Rancho Dominguez, Calif., 90220 USA) to remove buffer salts. The dialysis tubing contains approximately 0.15 L of the digested monoclonal antibody solutions is submerged in 4.0 L of water for 24 hours. The dialysis tubing is then moved into a new container containing 4.0 L of fresh water where it remained submerged for an additional 24 hours.

A MAB08 solution spiked with monoclonal antibody fragments is prepared from 18.0 mL of digested MAB II, 72.0 mL of undigested MAB08 in water, and 9.0 mL of 250 mM Tris at pH 7. The solution is then filtered through a 0.22 μm membrane (Stericup®-GP with a 0.22 μm Millipore Express® PLUS membrane, 250 mL, catalogue number: SCGPU02RE, EMD Millipore Corp. Billerica, Mass., 01821, USA).

Then 15 mL centrifuge tubes are loaded with 5 mg or 10 mg of MeadWestVaco Nuchar HD activated carbon (MeadWestVaco Corporation, Richmond, Va., USA), 10 mg of Norit Darco KB-G activated carbon (Norit Americas Inc., Marshall, Tex., USA), or 10 mg of Norit CGP Super activated carbon (Norit Americas Inc., Marshall, Tex., USA). A second set of 15 mL centrifuge tubes are loaded with 25 μL or 50 μL of either DVB hydrophobic resin or DVB-EGDMA hydrophobic resin. No media is added to a third set of set of 15 mL centrifuge tubes that is used as a control. Then 5.0 mL of the fragment spiked MAB08 solution containing 1.7% fragments is added to the centrifuge tubes. The tubes are allowed to rotate for 20 hours. Then all the tubes are subjected to centrifugation and filtered through a 0.22 micron membrane (Millex® Syringe Filter Units, Millex®-GV, 0.22 μm, PVDF, 33 mm, gamma sterilized, catalogue number: SLGV033RB, EMD Millipore Corporation, Billerica, Mass., 01821, USA) to remove any particles that might remain suspended in solution. The amount of the MAB08 remaining in the samples is determined by IgG quantification by Protein A HPLC. The percentage of fragments remaining in the samples is determined by size exclusion chromatography.

As summarized in Table 4 below, this experiment demonstrates that it is possible to selectively remove monoclonal antibody fragments from a solution containing the monoclonal antibody by static treatment with different types of activated carbon and different types of hydrophobic resin. As the amount of activated carbon or hydrophobic resin added to the monoclonal antibody solution is increased the percentage of fragments is reduced. The data indicate the unexpected result that both resins can be used to selectively remove monoclonal antibody fragments from a solution of a monoclonal antibody under static binding conditions.

TABLE 4

Recovery of monoclonal antibody and percentage of fragments after static treatment of MAB08 solutions with three different types of activated carbon and two different types of hydrophobic resins.

| media | amount of media | MAB08 concentration | MAB08 recovery | percentage of fragments |
|---|---|---|---|---|
| average of two controls | — | 7.86 | — | 1.72 |
| Nuchar HD | 10 mg | 7.75 | 99% | 0.73 |
| Nuchar HD | 20 mg | 7.60 | 97% | 0.34 |
| CGP Super | 10 mg | 7.53 | 96% | 1.08 |
| CGP Super | 20 mg | 7.57 | 96% | 0.66 |
| Darco KB-G | 10 mg | 7.73 | 98% | 1.01 |
| Darco KB-G | 20 mg | 7.76 | 99% | 0.47 |
| DVB-EGDMA resin | 25 µL | 7.36 | 94% | 1.41 |
| DVB-EGDMA resin | 50 µL | 7.60 | 97% | 1.11 |
| DVB resin | 25 µL | 7.66 | 98% | 1.07 |
| DVB resin | 50 µL | 7.52 | 96% | 0.62 |

Example 13

The Application of Hydrophobic Resins for the Removal of Monoclonal Antibody Fragments and HCP from a Solution of a Monoclonal Antibody Under Static Conditions This representative example demonstrates that both monoclonal antibody fragments and HCP can be selectively removed from a solution of a monoclonal antibody by static treatment with different types of hydrophobic resins.

Solutions of MAB04 are prepared with approximately 1.99% of monoclonal antibody fragments and 21 ppm of HCP. This solution is then treated with one of two different hydrophobic resins under static conditions, as described below.

MAB04 is produced by a CHO cell culture, and subjected to a Protein A chromatography capture process eluting the product with 50 mM acetate at pH 3.5. The solution pH is adjusted to pH 7.5 using 1.8 M Tris base and then filtered through a 0.22 µm membrane (Stericup®-GP with a 0.22 µm Millipore Express® PLUS membrane, 250 mL, catalogue number: SCGPU02RE, EMD Millipore Corp. Billerica, Mass., 01821, USA). The resulting solution is determined by size exclusion chromatography to have 1.99% of fragments determined by an ELISA HCP assay to have 21 ppm of HCP.

Then 15 ml centrifuge tubes are loaded with 12.5 µL, 25 µL or 50 µL of either cross-linked divinylbenzene (DVB) resin or cross-linked divinylbenzene-ethylene glycol dimethacrylate (DVB-EGDMA) resin. No media is added to a second set of 15 mL centrifuge tubes that is used as a control. Then 5.0 mL of the MAB04 solution containing 1.99% of fragments is added to the centrifuge tubes. The tubes are allowed to rotate for 24 hours. Then all the solutions are filtered through a 0.22 micron membrane (Millex® Syringe Filter Units, Millex®-GV, 0.22 µm, PVDF, 33 mm, gamma sterilized, catalogue number:SLGV033RB, EMD Millipore Corporation, Billerica, Mass., 01821, USA) to remove any resin particles that might remain suspended in solution. The concentration of the MAB04 remaining in the samples is determined by UV spectrophotometer at 280 nm. The percentage of fragments remaining in the samples is determined by size exclusion chromatography. The HCP concentration remaining in the samples is determined by an ELISA assay.

As summarized in Tables 5a and 5b below show the recovery of monoclonal antibody and the percentage of fragments in the solutions before treatment with the hydrophobic resins. The experiment demonstrates that static treatment of a monoclonal antibody solution with hydrophobic resins selectively removes monoclonal antibody fragments. As the amount of hydrophobic resin added to the monoclonal antibody solution is increased, the percentage of fragments remaining in the solution is reduced. The data indicate the unexpected result that hydrophobic resins can be used to selectively remove monoclonal antibody fragments from a solution of a monoclonal antibody under static binding conditions.

TABLE 5a

Recovery of monoclonal antibody and percentage of fragments after static treatment of MAB04 solution with a DVB-EG DMA hydrophobic resin.

| resin added (µL) | antibody recovery | HCP (ppm) | fragment percentage |
|---|---|---|---|
| 0 | — | 21 | 1.99% |
| 12.5 | 94% | 7 | 1.62% |
| 25.0 | 94% | 3 | 1.18% |
| 50.0 | 83% | 1 | 0.72% |

TABLE 5b

Recovery of monoclonal antibody and percentage of fragments after static treatment of MAB04 solution with a cross-linked cross-linked DVB hydrophobic resin.

| resin added (µL) | antibody recovery | HCP (ppm) | fragment percentage |
|---|---|---|---|
| 0 | — | 21 | 1.99% |
| 12.5 | >99% | 4 | 1.41% |
| 25.0 | 97% | 2 | 0.88% |
| 50.0 | 96% | 1 | 0.00% |

Example 14

The Application of Hydrophobic Resins for the Removal of Monoclonal Antibody Fragments and HCP from a Solution of a Monoclonal Antibody Under Static Conditions This representative example demonstrates that monoclonal antibody fragments can be selectively removed from a solution of a monoclonal antibody by static treatment with different types of hydrophobic resins.

Solutions of MAB05 are prepared with approximately 0.31% of monoclonal antibody fragments and 578 ppm of HCP. This solution is then treated with one of two different hydrophobic resins under static conditions, as described below.

MAB05 is produced by a CHO cell culture, and subjected to a Protein A chromatography capture process eluting the product with 50 mM acetate at pH 3.5. The solution pH is adjusted to pH 7.5 using 1.8 M Tris base and then filtered through a 0.22 µm membrane (Stericup®-GP with a 0.22 µm Millipore Express® PLUS membrane, 250 mL, catalogue number: SCGPU02RE, EMD Millipore Corp. Billerica, Mass., 01821, USA). The resulting solution is determined by size exclusion chromatography to have 0.31% of fragments and determined by an ELISA HCP assay to have 578 ppm of HCP.

Then 15 mL centrifuge tubes are loaded with 25 μL, 50 μL, or 100 μL of either cross-linked divinylbenzene (DVB) resin or cross-linked divinylbenzene-ethylene glycol dimethacrylate (DVB-EGDMA) resin. No media is added to a second of set of 15 mL centrifuge tubes that are used as a control. Then 5.0 mL of the MAB05 solution containing 1.99% of fragments is added to the centrifuge tubes. The tubes are allowed to rotate for 24 hours. Then all the solutions are filtered through a 0.22 micron membrane (Millex® Syringe Filter Units, Millex®-GV, 0.22 μm, PVDF, 33 mm, gamma sterilized, catalogue number: SLGV033RB, EMD Millipore Corporation, Billerica, Mass., 01821, USA) to remove any resin particles that might remain suspended in solution. The concentration of the MAB05 remaining in the samples is determined by UV spectrophotometer at 280 nm. The percentage of fragments remaining in the samples is determined by size exclusion chromatography. The HCP concentration remaining in the samples was determined by an ELISA assay.

As summarized in Table 6a, 6b and 6c below, it is shown the recovery of monoclonal antibody, the percentage of fragments, and the concentration of HCP in the solutions before treatment with the hydrophobic resins. The experiment demonstrates that static treatment of a monoclonal antibody solution with hydrophobic resins selectively removes monoclonal antibody fragments and HCP. As the amount of hydrophobic resin added to the monoclonal antibody solution is increased, the percentage of fragments remaining in the solution is reduced. The data indicate the unexpected result that hydrophobic resins can be used to selectively remove monoclonal antibody fragments and HCP from a solution of a monoclonal antibody under static binding conditions.

TABLE 6a

Recovery of monoclonal antibody and percentage of fragments after static treatment of MAB04 solution with a DVB-EGDMA hydrophobic resin.

| resin added (μL) | antibody recovery | HCP (ppm) | fragment percentage |
|---|---|---|---|
| 0 | — | 578 | 0.31% |
| 25 | 94% | 14 | 0.15% |
| 50 | 93% | 8 | 0.10% |
| 100 | 86% | 4 | BDL* |

*Below the limit of detection.

TABLE 6b

Recovery of monoclonal antibody and percentage of fragments after static treatment of MAB04 solution with a cross-linked DVB hydrophobic resin.

| resin added (μL) | antibody recovery | HCP (ppm) | fragment percentage |
|---|---|---|---|
| 0 | — | 578 | 0.31% |
| 25 | 97% | 12 | 0.12% |
| 50 | 93% | 4 | 0.03% |
| 100 | 87% | 4 | BDL* |

*Below the limit of detection.

TABLE 6c

Recovery of monoclonal antibody and percentage of fragments after static treatment with a cross-linked DVB hydrophobic resin at different pH and conductivity conditions.

| solution pH | conductivity [mS/cm] | DVB resin [μL] | antibody recovery [%] | percentage of fragments [%] |
|---|---|---|---|---|
| 4.0 | 4.5 | 0 | — | 1.50 |
| 4.0 | 4.5 | 50 | 90 | 0.00 |
| 4.0 | 22 | 0 | — | 1.49 |
| 4.0 | 22 | 50 | 82 | 0.16 |
| 5.0 | 4.5 | 0 | — | 1.70 |
| 5.0 | 4.5 | 50 | 92 | 0.12 |
| 5.0 | 22 | 0 | — | 1.52 |
| 5.0 | 22 | 50 | 89 | 0.15 |
| 6.0 | 4.5 | 0 | — | 1.69 |
| 6.0 | 4.5 | 50 | 88 | 0.35 |
| 6.0 | 22 | 0 | — | 1.54 |
| 6.0 | 22 | 50 | 83 | 0.12 |
| 7.0 | 4.5 | 0 | — | 1.53 |
| 7.0 | 4.5 | 50 | 88 | 0.24 |
| 7.0 | 22 | 0 | — | 1.52 |
| 7.0 | 22 | 50 | 84 | 0.11 |
| 8.0 | 4.5 | 0 | — | 1.74 |
| 8.0 | 4.5 | 50 | 86 | 0.22 |
| 8.0 | 22 | 0 | — | 1.68 |
| 8.0 | 22 | 50 | 83 | 0.12 |
| 9.0 | 4.5 | 0 | — | 1.72 |
| 9.0 | 4.5 | 50 | 87 | 0.17 |
| 9.0 | 22 | 0 | — | 1.69 |
| 9.0 | 22 | 50 | 83 | 0.15 |

Example 15

The Application of Hydrophobic Resins for the Removal of HCP from Various Post Prot a Solutions of a Monoclonal Antibody Under Dynamic Conditions In this experiment, particulate material consisting of poly(ethyl)styrene (m), crosslinked with divinylbenzene (PS-DVB) (70%) and ethylene glycol dimethylacrylate (PS-DVB-EGDMA) (30%) copolymers was evaluated for its ability to remove HCP from various antibody post Protein A pools. The post Prot A pools are generated using commercially available Prosep® Ultra Plus or Mab Select Sure® or Eshmuno® A materials, where clarified cell culture containing antibody of interest is loaded on re-equilibrated Prot A column to 40 mg/ml binding capacity values @ 600 cm/h and then washed with re-equilibration buffer and 0.5M NaCl solution for 5 CV following be the 5 CV elution using 50 mM Glycyne and 50 mM Acetic acid buffer at pH 3.5. The collected pools are then charged to the particulate material consisting of poly(ethyl)styrene (m), crosslinked with divinylbenzene (PS-DVB) (70%) and ethylene glycol dimethylacrylate (PS-DVB-EGDMA) (30%) copolymers. Measurements are performed in dynamic mode, of packing the particulate material in the chromatographic column and charging it with antibody post Protein A feed (pH 5.0) @ 600 cm/h after equilibration with 50 mM Acetate buffer pH 5.0, LF ~2 mS/cm for at >20 CV. Antibody levels were quantified via SEC-HPLC an d HCP amount via ELISA measurements (see FIG. 10):

FIG. 10a: HCP levels in various mAb03 post Protein A (e.g. Prosep® Ultra Plus (PUP), Mab Select Sure®, Eshmuno® A) pools after different loadings on PS-DVB-EGDMA particulate material, where this material consists of poly(ethyl)styrene (m), crosslinked with divinylbenzene (70%) and ethylene glycol dimethylacrylate (30%) copolymers.

FIG. 10b: HCP levels in various mAb07 post Protein A (e.g. Prosep® Ultra Plus (PUP), Mab Select Sure®, Eshmuno® A) pools after different loadings on PS-DVB-EGDMA particulate material, where this material consists of poly(ethyl)styrene (m), crosslinked with divinylbenzene (70%) and ethylene glycol dimethylacrylate (30%) copolymers.

Example 16

The Application of Hydrophobic Resins for the Removal of HCP from Salt Containing Post Prot a Solutions of a Monoclonal Antibody Under Dynamic Conditions In the following experiment particulate material, consisting of poly(ethyl)styrene (m), crosslinked with divinylbenzene (PS-DVB) (70%) and ethylene glycol dimethylacrylate (PS-DVB-EGDMA) (30%) copolymers is evaluated for their ability to remove HCP from salt containing post Protein A antibody pools. Measurements are performed in dynamic mode, of packing the particulate material in the chromatographic column and charging it with salt containing (e.g. 0.5 m NaCl) antibody post Protein A feed (pH 5.0) @ 600 cm/h after equilibration with 50 mM Acetate buffer pH 5.0, LF ~2 mS/cm for at >20 CV. Antibody levels are quantified via SEC-HPLC and HCP amount via Elisa measurements (see FIG. 11):

FIG. 11: mAb03 HCP break through levels at different loadings for PS-DVB EGDMA particulate material, where in one experiment NaCL was added to 0.5M concentration. 30451 material consists of polystyrene (m), crosslinked with divinylbenzene copolymers, 30410 material consists of polystyrene (m), crosslinked with divinylbenzene (70%) and ethylene glycol dimethylacrylate (30%) copolymers.

Example 17

In this experiment, particulate material consisting of poly (ethyl)styrene (m), crosslinked with divinylbenzene (PS-DVB) (70%) and ethylene glycol dimethylacrylate (PS-DVB-EGDMA) (30%) copolymers is evaluated in comparison to commercially available hydrophobic material for their ability to remove HCP from various antibody post Protein A pools. Measurements are performed in dynamic mode, of packing the particulate material in the chromatographic column and charging it with post Protein A antibody feed (pH 5.0) @ 900 cm/h after equilibration with 50 mM Acetate buffer pH 5.0, LF ~2 mS/cm for at >20 CV. Antibody levels are quantified via SEC-HPLC and HCP amount via ELISA measurements (see FIG. 12):

FIG. 12: mAb03 HCP break through levels at different loadings for PS-DVB-EGDMA particulate material, where 30410 material consists of poly(ethyl)styrene (m), crosslinked with divinylbenzene (70%) and ethylene glycol dimethylacrylate (30%) copolymers. P242 is competitor hydrophobic material, P248 is competitor hydrophobic material.

Example 18

The Application of PS-DVB-EGDMA Resin for the Removal of Protein A Under Static Conditions This example demonstrates that Protein A can be selectively removed from a solution by static treatment with PS-DVB-EGDMA resin at various pH conditions.

Two solutions containing Protein A are prepared:
a) approximately 2 mg/ml of Protein A is dissolved in 25 mM acetate-phosphate buffer containing 50 mM NaCl pH 4.00
b) approximately 2 mg/ml of Protein A is dissolved in 50 mM TRIS buffer containing 50 mM NaCl pH 8.00.

The prepared solutions are then filtered through a 0.22 µm membrane (Stericup®-GP with a 0.22 µm Millipore Express® PLUS membrane, 250 mL, catalogue number: SCGPU02RE, EMD Millipore Corp. Billerica, Mass., 01821, USA) and then are treated with one of three different types of resins (e.g. DVB-EGDMA resin, Eshmuno® S, Eshmuno® Q) under static conditions, as described below.

1.5 ml Eppendorf vials are loaded with 200 µl of PS-DVB-EGDMA resin, 200 µl Eshmuno® S, 200 µl Eshmuno® Q (Merck KGaA, Darmstadt, Germany). Then 1 mL of the prepared Protein A solution is added to the prepared Eppendorf vials. The vials are allowed to shake for 20 hours. Then all the tubes are subjected to centrifugation and filtered through a 0.22 micron membrane (Millex® Syringe Filter Units, Millex®-GV, 0.22 µm, PVDF, 33 mm, gamma sterilized, catalogue number:SLGV033RB, EMD Millipore Corporation, Billerica, Mass., 01821, USA) to remove any beads that might remain suspended in solution. The amount of the Protein A remaining in the samples is determined by photometric adsorption at 280 nm and additionally subjected to the SDS-Page analysis.

As summarized in Table 7 below, this experiment demonstrates that it is possible to selectively adsorb Protein A from a solution adjusted to different pH values by static treatment with different types of beads. As the Eshmuno® S adsorbed Protein A at pH 4.00 solution, it failed to adsorb Protein A at pH 8.00 solution. Additionally Eshmuno® Q was able to adsorb Protein A at pH 8.00 solution, but failed in pH 4.00. Surprisingly, the data indicates the unexpected result that PS-DVB-EGDMA resin is able to adsorb Protein A in pH 4.00 and pH 8.00 solutions under static binding conditions.

TABLE 7

Protein A levels after static treatment with three different resin types at two different pH conditions.

| media | amount of media | pH | UV adsorption of solution after static binding | Protein A concentration in solution after static binding [mg/ml] |
| --- | --- | --- | --- | --- |
| Starting conditions | — | 4.00 | 0.343 | 2.05 |
| Starting conditions | — | 8.00 | 0.325 | 1.95 |
| Eshmuno ® S | 200 µl | 4.00 | 0.001 | 0.01 |
| Eshmuno ® S | 200 µl | 8.00 | 0.313 | 1.87 |
| Eshmuno ® Q | 200 µl | 4.00 | 0.373 | 2.23 |
| Eshmuno ® Q | 200 µl | 8.00 | 0.052 | 0.31 |
| PS-DVB-EGDMA resin | 200 µl | 4.00 | 0.026 | 0.16 |
| PS-DVB-EGDMA resin | 200 µl | 8.00 | 0.022 | 0.13 |

FIG. 13: Reduced SDS PAGE analysis of Protein A adsorption on DVB-EGDMA, Eshmuno® S, and Eshmuno® Q resins according to Example 18 with
M=PerfectProtein™ Marker,
PA=Starting Solution (2 mg/ml Protein A),
S=supernatant after adsorption @ Eshmuno®S,
Q=supernatant after adsorption @ Eshmuno®Q,
P=supernatant after adsorption @ DVB-EGDMA Example 19

The Application of Hydrophobic Resins for the Removal of HCP from Post Prot a Solutions of a Monoclonal Antibody Under Dynamic Conditions in Combination with Ion Exchange Materials In this experiment, particulate material consisting of poly(ethyl)styrene (m), crosslinked with divinylbenzene (PS-DVB) (70%) and ethylene glycol dimethylacrylate (PS-DVB-EGDMA) (30%) copolymers (686.75 m²/g surface area, 14 nm average pore size, and 41 μm average particle size) is evaluated for its ability to remove HCP from post Protein A antibody pools. The post Prot A pools are generated using commercially available Prosep® Ultra Plus, where clarified cell culture containing antibody of interest is loaded on re-equilibrated Prot A column to 40 mg/ml binding capacity values @ 600 cm/h and then washed with re-equilibration buffer for 5 CV following the 5 CV elution using 50 mM Glycyne and 50 mM Acetic acid buffer at pH 3.5. The collected pools are then charged to the particulate material consisting of poly(ethyl)styrene (m), crosslinked with divinylbenzene (PS-DVB) (70%) and ethylene glycol dimethylacrylate (PS-DVB-EGDMA) (30%) copolymers, Eshmuno®CPX, Eshmuno®Q individually and in combination, directly connecting all devices. Measurements are performed in dynamic mode, of packing the particulate material in the chromatographic column and charging it with antibody post Protein A feed (pH 6.75, conductivity~2.7 mS/cm, ~1000 ng/mlHCP amount) @ 600 cm/h after equilibration with 20 mM Phosphate buffer pH 6.75, LF ~4 mS/cm for at >20 CV. In case of combined example, all devices were connected one after another in a sequence of: PS-DVB-EGDMA followed by Eshmuno®CPX followed by Eshmuno®Q. Antibody levels were quantified via SEC-HPLC an d HCP amount via ELISA measurements (see Table 8):

TABLE 8

HCP levels (ppm) after dynamic treatment with three different resin types individually and combined.

| | HCP level (ppm) after dynamic treatment with various materials | | | |
|---|---|---|---|---|
| Loading (mg/ml)* | PS-DVB-EGDMA resin | Eshmuno® CPX | Eshmuno® Q | All combined in one |
| 350 | 39.8 | 72.14 | 11.17 | 1.73 |
| 500 | 49.8 | 63.27 | 12.49 | 2.14 |
| 650 | 44.2 | 73.27 | 10.39 | 2.3 |
| 750 | 55.6 | 78.30 | 12.86 | 2.36 |
| 900 | 123.6 | 89.7 | 10.29 | 2.83 |
| 1200 | — | — | — | 3.05 |
| 1500 | — | — | — | 3.09 |

*antibody loadings calculated per resin volume. In case of combined example, all used columns had the same volume, but the loading accounts for the first column (PS-DVB_EGDMA resin).

What is claimed:

1. A method for the separation of host cell proteins, antibody fragments and low molecular weight substances from solutions containing antibodies, said method comprising:
contacting a solution containing antibodies with a hydrophobic chromatography material for a period of time whereby the antibodies stay in solution and host cell proteins, antibody fragments and low molecular weight substances are adsorbed by the hydrophobic chromatography material,
wherein said hydrophobic chromatography material is a particulate material consisting of polystyrene or poly(ethyl)styrene, which is cross-linked with copolymer of divinylbenzene and ethyleneglycol methacrylate in a ratio of 98:2 up to 10:90% by weight.

2. The method of claim 1, wherein said solution containing antibodies is an aqueous solution having a pH value in the range of 2-11 and a conductivity in the range of 1-150 mS/cm.

3. The method of claim 1, wherein said solution containing antibodies is an aqueous solution, and said aqueous solution is passed through at a flow rate in the range of 150-1000 cm/min.

4. The method of claim 1, wherein the separation is processed after a Protein A affinity binding step.

5. The method of claim 1, further comprising contacting the solution with an ion exchange resin.

6. The method of claim 1, wherein said particulate material has mean particle diameters in the range of 10 μm to 600 μm.

7. The method according to claim 6, wherein said hydrophobic chromatography material has pore sizes in the range of 4-500 nm.

8. The method of claim 1, wherein said hydrophobic chromatography material has pore sizes in the range of 4-500 nm.

9. The method of claim 1, further comprising contacting said solution with an ion exchange resin, specific for the separation of Protein A, resulting in a depletion of up to <10 ng host cell proteins and removal of leached Protein A.

10. The method according to claim 9, wherein said hydrophobic chromatography material is hydrophobic polymer beads.

11. The method of claim 1, wherein said solution containing antibodies is an aqueous solution having a pH value in the range of 5-9 and a conductivity in the range of 2-50 mS/cm.

12. The method of claim 1, wherein said solution containing antibodies is an aqueous solution, and said aqueous solution is passed through at a flow rate in the range of 300-900 cm/min.

13. The method of claim 1, wherein said particulate material has mean particle diameters in the range of 20 μm to 150 μm.

14. The method of claim 1, wherein said a particulate material has mean particle diameters in the range of 20 μm to 63 μm.

15. The method of claim 1, wherein said hydrophobic chromatography material has pore sizes in the range of 10-30 nm.

16. The method of claim 1, wherein said hydrophobic chromatography material has pore sizes in the range of 13 nm to 25 nm.

17. The method of claim 1, wherein said hydrophobic chromatography material is rigid hydrophobic porous polymer beads having mean particle diameters in the range of 10 μm to 600 μm with pore sizes in the range of 4-500 nm.

18. A method for the separation of host cell proteins, antibody fragments and low molecular weight substances from solutions containing antibodies, said method comprising:
contacting a solution containing antibodies with a hydrophobic chromatography material for a period of time whereby the antibodies stay in solution and host cell proteins, antibody fragments and low molecular weight substances are adsorbed by the hydrophobic chromatography material, wherein said hydrophobic chromatography material is poly(ethyl)styrene crosslinked with divinylbenzene or poly(ethyl)styrene crosslinked with divinylbenzene and ethylene glycol dimethylacrylate.

19. A method for the separation of host cell proteins, antibody fragments and low molecular weight substances from solutions containing antibodies, said method comprising:

contacting a solution containing antibodies with a hydrophobic chromatography material for a period of time whereby the antibodies stay in solution and host cell proteins, antibody fragments and low molecular weight substances are adsorbed by the hydrophobic chromatography material, wherein said hydrophobic chromatography material is hydrophobic polymer beads consisting of cross-linked vinylbenzene, poly(ethyl)styrene-divinylbenzene, or polystyrene-divinylbenzene ethyleneglycol-dimethylacrylate resin.

\* \* \* \* \*